US011668711B2

(12) United States Patent
Mehta et al.

(10) Patent No.: US 11,668,711 B2
(45) Date of Patent: Jun. 6, 2023

(54) MULTIPLEXED DIAGNOSTIC ASSAY FOR IRON AND VITAMIN A DEFICIENCY AND METHODS OF USE THEREOF

(71) Applicant: CORNELL UNIVERSITY, Ithaca, NY (US)

(72) Inventors: Saurabh Mehta, Ithaca, NY (US); David Erickson, Ithaca, NY (US); Zhengda Lu, Ithaca, NY (US)

(73) Assignee: CORNELL UNIVERISTY, Ithaca, NY (US)

( * ) Notice: Subject to any disclaimer, the term of this patent is extended or adjusted under 35 U.S.C. 154(b) by 51 days.

(21) Appl. No.: 16/763,707

(22) PCT Filed: Nov. 13, 2018

(86) PCT No.: PCT/US2018/060789
§ 371 (c)(1),
(2) Date: May 13, 2020

(87) PCT Pub. No.: WO2019/094950
PCT Pub. Date: May 16, 2019

(65) Prior Publication Data
US 2020/0300850 A1    Sep. 24, 2020

Related U.S. Application Data

(60) Provisional application No. 62/585,275, filed on Nov. 13, 2017.

(51) Int. Cl.
*G01N 33/543* (2006.01)
*G01N 21/64* (2006.01)
(Continued)

(52) U.S. Cl.
CPC ... *G01N 33/54388* (2021.08); *G01N 21/6428* (2013.01); *G01N 33/54386* (2013.01);
(Continued)

(58) Field of Classification Search
CPC ........... G01N 33/54388; G01N 33/558; G01N 2470/04; G01N 2480/10; G01N 33/82;
(Continued)

(56) References Cited

U.S. PATENT DOCUMENTS

2005/0176032 A1* 8/2005 Breslauer ............. C12Q 1/6818
435/6.1
2008/0197019 A1* 8/2008 Santiago ........... G01N 27/44726
204/549

(Continued)

FOREIGN PATENT DOCUMENTS

WO    2017/087831 A1    5/2017
WO    2017/087834 A1    5/2017

OTHER PUBLICATIONS

Brindle et al. A Multiplex Immunoassay Method for Simultaneous Quantification of Iron, Vitamin A and Inflammation Status Markers, PLoS ONE 9(12) pp. 1-22 (Year: 2014).*
(Continued)

*Primary Examiner* — Melanie Brown
(74) *Attorney, Agent, or Firm* — Troutman Pepper Hamilton Sanders LLP (Rochester)

(57) ABSTRACT

A diagnostic assay strip includes a first layer that includes an iron mobile labelled specific binding partner that will bind to and iron biomarker from a sample and produce an iron complex and a vitamin A mobile labelled specific binding partner that will bind to a vitamin A biomarker from the sample and produce a vitamin A complex. A second layer includes iron and vitamin A test regions, and a control region. The iron test region has immobilized specific binding partners that will bind to the iron complex. The vitamin A test region has immobilized vitamin A biomarker that will bind to vitamin A mobile labelled specific binding partner, which is not bound to the vitamin A biomarker, passing from the first layer to the second layer. The control region has a
(Continued)

moiety which will non-specifically bind to and immobilize the iron and vitamin A labelled specific binding partners. Methods of using the diagnostic assay strip are also discussed.

42 Claims, 13 Drawing Sheets

(51) Int. Cl.
    *G01N 33/58*     (2006.01)
    *G01N 33/68*     (2006.01)
    *G01N 33/82*     (2006.01)
    *G01N 33/84*     (2006.01)

(52) U.S. Cl.
    CPC ....... *G01N 33/582* (2013.01); *G01N 33/6803* (2013.01); *G01N 33/82* (2013.01); *G01N 33/84* (2013.01); *G01N 2021/6441* (2013.01); *G01N 2333/4737* (2013.01); *G01N 2333/705* (2013.01); *G01N 2458/00* (2013.01); *G01N 2470/04* (2021.08); *G01N 2470/10* (2021.08)

(58) Field of Classification Search
    CPC ........... G01N 33/84; G01N 2333/4737; G01N 2333/705
    See application file for complete search history.

(56) References Cited

U.S. PATENT DOCUMENTS

| | | | |
|---|---|---|---|
| 2008/0199851 A1* | 8/2008 | Egan | B01L 3/5029 435/5 |
| 2009/0122311 A1* | 5/2009 | Kanda | G01N 21/645 356/318 |
| 2010/0267065 A1* | 10/2010 | Geiger | C12Q 1/56 435/13 |
| 2011/0195422 A1 | 8/2011 | Selinfreund et al. | |
| 2012/0309636 A1* | 12/2012 | Gibbons | C12Q 1/48 435/6.12 |
| 2015/0293085 A1* | 10/2015 | Anderberg | G01N 33/54386 506/9 |

OTHER PUBLICATIONS

Lee et al. NutriPhone: a mobile platform for low-cost point-of-care quantification of vitamin B12 concentrations, Scientific reports, vol. 6, 28237, pp. 1-8 (Year: 2016).*
International Search Report and Written Opinion for corresponding Application No. PCT/US2018/060789 (dated Feb. 1, 2019).
Brindle et al., "Simultaneous Assessment of Iodine, iron, Vitamin A, Malarial Antigenemia, and Inflammation Status Biomarkers via a Multiplex Immunoassay Method of a Population of Pregnant Women from Niger," PLoS ONE 12 (1):1-20 (2017).

* cited by examiner

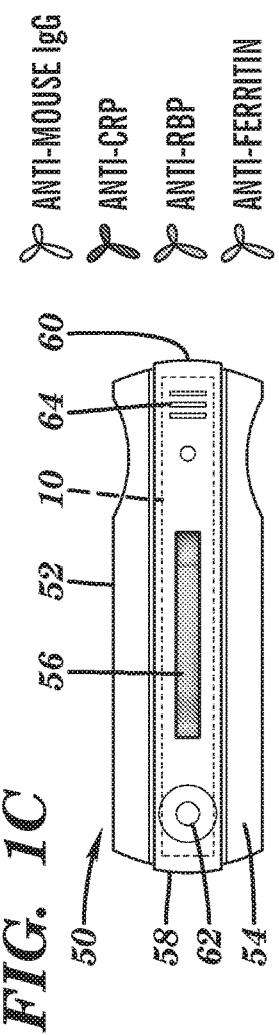

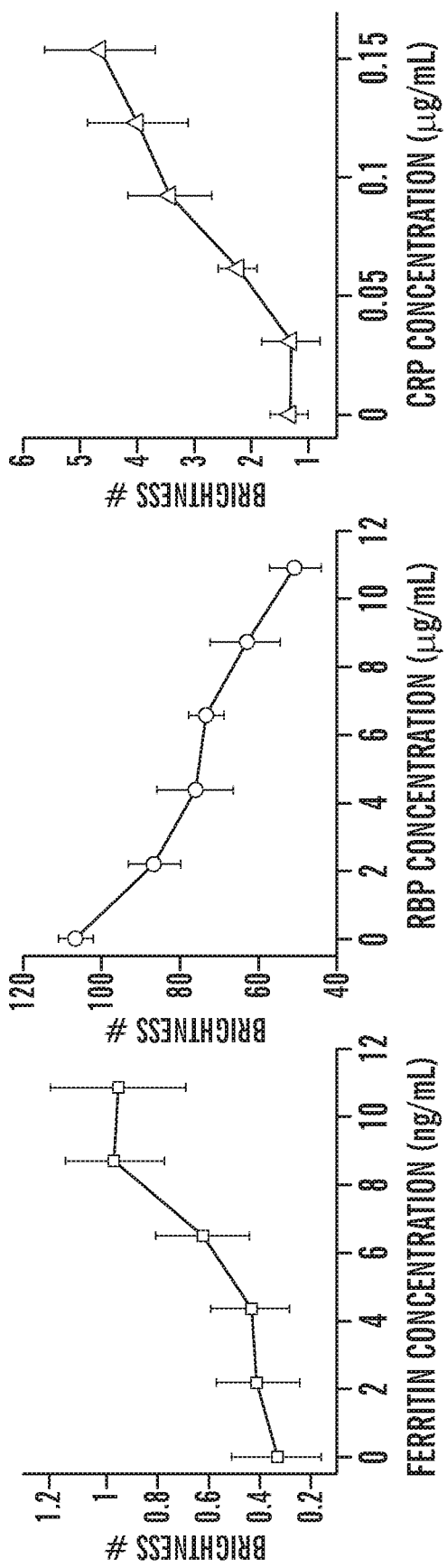

MULTIPLEXED DIAGNOSTIC ASSAY FOR IRON AND VITAMIN A DEFICIENCY AND METHODS OF USE THEREOF

This application is a national stage application under 35 U.S.C. § 371 of PCT Application No. PCT/US2018/060789, filed Nov. 13, 2018, which claims the priority benefit of U.S. Provisional Patent Application Ser. No. 62/585,275 filed Nov. 13, 2017, which are hereby incorporated by reference in their entirety.

GOVERNMENT FUNDING

This invention was made with government support under Grant Number 1343058 awarded by National Science Foundation and Grant Number 1R01EB021331 awarded by National Institutes of Health. The government has certain rights in the invention.

FIELD OF THE INVENTION

The present invention relates to a multiplexed diagnostic assay for iron and vitamin A deficiency and methods of use thereof.

BACKGROUND OF THE INVENTION

Iron deficiency and vitamin A deficiency are two of the most prevalent micronutrient deficiencies worldwide. Iron deficiency affects 2 billion people and is a common cause of anemia, which may reduce physical work capacity in adults or lead to impaired brain development in children. Vitamin A deficiency causes night blindness, mostly among children and pregnant women, affecting about 29% of the population in low and mid-income countries. Vitamin A deficiency also negatively affects the immune system and results in lowered erythropoiesis. Moreover, iron deficiency and vitamin A deficiency often coexist, with the interaction between the two possibly exacerbating each other.

Therefore, simultaneous access to iron and vitamin A status among populations at risk is important. Iron deficiency and vitamin A deficiency due to dietary inadequacy can be relatively effectively treated at early stages, although challenging at population-level, by changing diet and/or taking supplements. Measuring iron deficiency and vitamin A deficiency status represents an important first step in managing these deficiencies. Many efforts to prevent or treat these deficiencies are hampered by the lack of adequate, accessible, and affordable diagnostic methods that can enable better targeting of interventions.

Over the past decades, lateral flow immunochromatography assays have been widely adopted for diagnosing various diseases and medical conditions in point-of-care settings. These assays are rapid, simple, and produce colorimetric signals that can be interpreted by untrained personnel. However, rapid immunoassay tests for multiple targets are challenging. Current rapid diagnostic tests usually label multiple types of conjugation antibodies with the same optical tags (latex beads or colloidal gold nanoparticles), thus cross binding can be difficult to distinguish.

The present invention is directed to overcoming these and other deficiencies in the art.

SUMMARY OF THE INVENTION

One aspect of the present invention relates to a multiplexed diagnostic assay strip for detection of an iron biomarker and a vitamin A biomarker in a sample. The strip includes an elongate substrate extending between a first end at which the sample is applied to the strip and a second end at which results of the assay can be assessed. A first layer is supported on the elongate substrate proximate to the first end of the strip for receiving a liquid sample. The first layer includes an iron mobile labelled specific binding partner that will bind specifically to the iron biomarker from the sample applied to the first layer and produce an iron complex of the iron biomarker bound to the iron labelled specific binding partner. The first layer also includes a vitamin A mobile labelled specific binding partner that will specifically bind to the vitamin A biomarker from the sample applied to the first layer and produce a vitamin A complex of the vitamin A biomarker bound to the vitamin A labelled specific binding partner. A second layer is supported on the elongate substrate proximate to the second end of the strip and downstream of the first layer. The second layer includes an iron test region, a vitamin A test region, and a control region separated from each of the iron test region and the vitamin A test region. The iron test region has immobilized specific binding partners that will specifically bind to the iron complex and immobilize the iron complex in the iron test region. The vitamin A test region has immobilized vitamin A biomarker that will bind to vitamin A mobile labelled specific binding partner, which is not bound to the vitamin A biomarker, passing from the first layer to the second layer and immobilize the unbound vitamin A mobile labelled specific binding partner in the vitamin A test region. The control region has an immobilized moiety which will non-specifically bind to and immobilize the iron labelled specific binding partner and the vitamin A labelled specific binding partner in the control region.

Another aspect of the present invention relates to a diagnostic assay cartridge including the multiplexed diagnostic assay strip according to the present invention. The diagnostic assay cartridge includes an elongate housing having walls defining a chamber in which the multiplexed diagnostic assay strip is positioned. The cartridge extends between a first end proximate to the first end of the elongate substrate, where the sample is inserted through an inlet passage in a wall of the housing and into the chamber, and a second end proximate to the second end of the elongate substrate at which results of the assay can be assessed.

Yet another aspect of the present invention relates to a method of conducting a diagnostic assay. The method includes providing a multiplexed diagnostic assay strip in accordance with the present invention. A sample is applied to the first layer. A buffer is applied to a buffer pad located upstream of the first layer after applying the sample to the first layer, whereby the buffer causes flow of material from the first end of the elongate substrate to the second end of the elongate substrate. The test and control regions in the second layer are analyzed to determine whether the iron biomarker or the vitamin A biomarker are present in the sample and/or what quantity of the iron biomarker or the vitamin A biomarker is present.

The present invention provides a rapid diagnostic test and mobile enabled platform for simultaneously quantifying iron (ferritin), vitamin A (retinol-binding protein), and inflammation (C-reactive protein) status. The test advantageously combines multiple florescent markers and immunoassay approaches on a single test that allows for rapid and accurate quantification of iron, vitamin A, and inflammation status. Measuring these targets on the same test device is difficult as the physiological range of the individual markers of interest varies over five (5) orders of magnitude. Thus, results for a test for each of the markers at the same time can be difficult to obtain. The present invention solves this difficulty through the use of the multiple fluorescent markers and various immunoassay approaches applied on the single device. Further, analysis of raw image date removes errors that additionally help to detect all three markers on the same test device.

This technology is suitable for point-of-care use in both resource-rich and resource-limited settings. The system could have significant impact in areas of the world with high instances of micronutrient deficiencies, by providing a rapid, easy-to-operate tool for population-level micronutrient status surveys in situations that both iron deficiency and vitamin A deficiency need to be diagnosed.

BRIEF DESCRIPTION OF THE DRAWINGS

FIG. 1A is a perspective view of an embodiment of a multiplexed diagnostic assay strip of the present invention.

FIG. 1C is a top view of an embodiment of a diagnostic assay cartridge for housing the multiplexed assay strip of FIG. 1A.

FIGS. 5C-5E illustrate the Limit of detection for each marker in multiplex tests.

DETAILED DESCRIPTION OF THE INVENTION

Figure 1B:
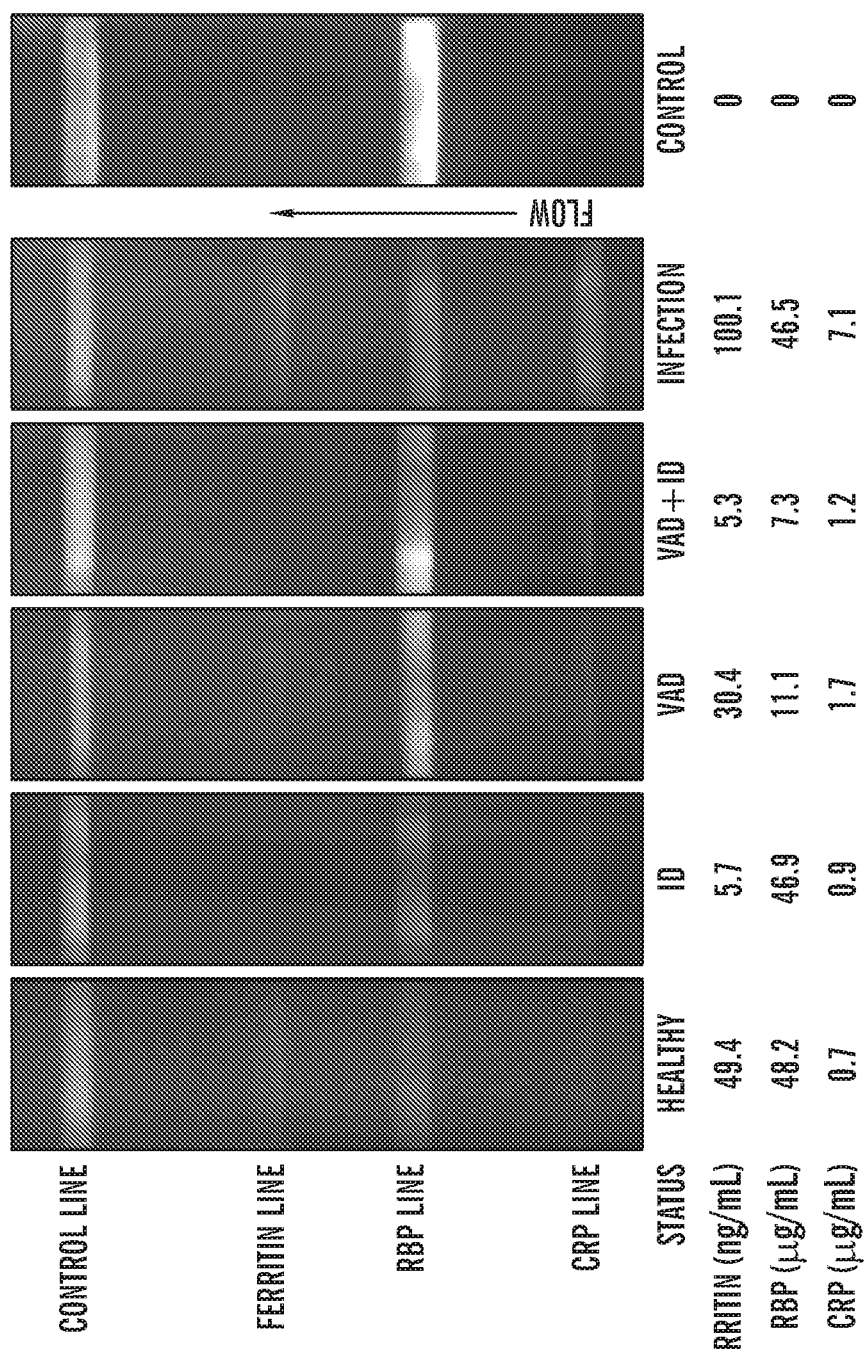
FIG. 1B is sample fluorescence image for the multiplexed diagnostic assay strip of the present invention.

The present invention relates to diagnostic assays. More specifically, the present invention relates to a multiplexed diagnostic assay strip for simultaneous detection of an iron biomarker and a vitamin A biomarker in a sample, a diagnostic assay cartridge including the multiplexed diagnostic assay strip, and a method of conducting a diagnostic assay.

One aspect of the present invention relates to a multiplexed diagnostic assay strip for detection of an iron biomarker and a vitamin A biomarker in a sample. The strip includes an elongate substrate extending between a first end at which the sample is applied to the strip and a second end at which results of the assay can be assessed. A first layer is supported on the elongate substrate proximate to the first end of the strip for receiving a liquid sample. The first layer includes an iron mobile labelled specific binding partner that will bind specifically to the iron biomarker from the sample applied to the first layer and produce an iron complex of the iron biomarker bound to the iron labelled specific binding partner. The first layer also includes a vitamin A mobile labelled specific binding partner that will specifically bind to the vitamin A biomarker from the sample applied to the first layer and produce a vitamin A complex of the vitamin A biomarker bound to the vitamin A labelled specific binding partner. A second layer is supported on the elongate substrate proximate to the second end of the strip and downstream of the first layer. The second layer includes an iron test region, a vitamin A test region, and a control region separated from each of the iron test region and the vitamin A test region. The iron test region has immobilized specific binding partners that will specifically bind to the iron complex and immobilize the iron complex in the iron test region. The vitamin A test region has immobilized vitamin A biomarker that will bind to vitamin A mobile labelled specific binding partner, which is not bound to the vitamin A biomarker, passing from the first layer to the second layer and immobilize the unbound vitamin A mobile labelled specific binding partner in the vitamin A test region. The control region has an immobilized moiety which will non-specifically bind to and immobilize the iron labelled specific binding partner and the vitamin A labelled specific binding partner in the control region.

FIG. 1A is a perspective view of a first embodiment of multiplexed diagnostic assay strip 10 of the present invention. Multiplexed diagnostic assay strip 10 may be utilized for simultaneous detection of an iron biomarker and a vitamin A biomarker in a sample (S), such as a blood sample, a plasma sample, a serum sample, a urine sample, a saliva sample, a sweat sample, cerebral spinal fluid, or tears. In this example, the iron biomarker is ferritin, which servers to store and transport iron in blood and can serve as an indicator of iron deficiency. The vitamin A biomarker is a retinol binding protein (RBP). Nearly all retinol, the circulating form of vitamin A in serum, is bound to RBP, so RBP concentrations in blood can be used as an indicator of vitamin A status.

Multiplexed diagnostic assay strip 10 may also be utilized for simultaneous detection of an inflammation biomarker in the sample (S), while also detecting ferritin and RBP. A challenge to diagnosing iron deficiency and vitamin A deficiency is that RBP and ferritin are both acute phase proteins. This means that RBP concentrations in blood can be temporarily reduced and ferritin concentrations can be temporarily increased by acute infection and inflammation. Therefore, readings taken during acute infection or inflammation periods can result in a false deficiency/sufficiency diagnosis. In this example, the inflammation biomarker is a C-reactive protein (CRP), or other similar marker of inflammation. Multiplexed diagnostic assay strip 10 can be utilized to simultaneously determine the presence of the iron biomarker (ferritin) and the vitamin A biomarker (RBP) to determine whether the patient has an iron and/or vitamin A deficiency. The measurement of inflammation biomarker (CRP) serves to determine whether inflammation, such as through an infection, impacts the results of the test.

As shown in FIG. 1A, multiplexed diagnostic assay strip 10 may be housed in diagnostic assay cartridge 50 as described in further detail below.

Multiplexed diagnostic assay strip 10 includes substrate 12, buffer pad 14, first layer 16, second layer 18, optional spacer layer 20, and collection layer 22. Multiplexed diagnostic assay strip 10 may also include other types or numbers of layers. Non-limiting examples of additional elements and configurations include those described in U.S. Patent Application Publication No. 2018/0273888 and PCT Patent Application WO2017/059436, the disclosures of which are hereby incorporated by reference in their entirety herein.

In one example, multiplexed diagnostic assay strip 10 is configured to be utilized in conjunction with a smartphone as described in U.S. Patent Application Publication No. 2016/0080548 and PCT Patent Application PCT/US14/12263, the disclosures of which are hereby incorporated by reference in their entirety herein. Specifically, multiplexed diagnostic assay strip 10 may be inserted into a smartphone accessory that provides for analysis of multiplexed diagnostic assay strip 10. The smartphone receives image data from the smartphone accessory to provide a quantification of the results of the diagnostic assay. In another example, multiplexed diagnostic assay strip 10 is configured to be utilized with the exemplary reader device illustrated in FIGS. 2A, 2B, and 2D and as described in further detail below.

Substrate 12 has an elongate form extending between first end 30 at which the sample (S) is applied to multiplexed diagnostic assay strip 10 and second end 32 at which results of the assay can be assessed. Substrate 12 is configured to support the various layers of multiplexed diagnostic assay strip 10 as described below. In one example, substrate 12 is a Flow Plus 180 Membrane Card (EMD Millipore, Billerica, Mass.) with a 2 mm clear polyester film backing to which the layers described below may be adhesively attached, by way of example, although other suitable substrates may be utilized.

Buffer pad 14 is supported on substrate 12 proximate to first end 30 of multiplexed diagnostic assay strip 10. Buffer pad 14 is configured to receive a buffer solution and pass the solution through to first layer 16 to generate a flow of materials between first layer 16 and second layer 18. Buffer pad 14 is positioned partially on top of first layer 16 to increase the flow of the buffer solution applied to buffer pad 14 to first layer 16.

First layer 16 is supported on substrate 12, distal from both first end 30 and second end 32 of substrate 12 and downstream of buffer pad 14, which is configured to receive and pass a buffer solution to first layer 16 to initiate a flow of materials from first layer 16 to second layer 18, as described below. A portion of first layer 16 is overlapped by buffer pad 14 to enhance fluid flow between buffer pad 14 and first layer 16.

In one example, first layer 16 is made of glass fibers, although other suitable materials may be utilized. First layer 16 provides a membrane for receiving a liquid sample (S), such as capillary blood from a finger stick. First layer 16 also provides a conjugate pad for storing antibody conjugates, as described below. Although in this example first layer 16 serves as both a sample and conjugate pad, in other examples separate sample and conjugate pads can be utilized such as described in U.S. Patent Application Publication No. 2018/0273888 and PCT Patent Application WO2017/059436, the disclosures of which are hereby incorporated by reference in their entirety herein.

First layer 16 includes iron mobile labelled specific binding partner 34 and vitamin A mobile labelled specific binding partner 35 located therein, although first layer 16 may include other conjugates such as inflammation mobile binding partner 36 as well.

Iron mobile labelled specific binding partner 34 is selected to be a binding partner of the iron biomarker, such as ferritin, such that iron mobile labelled specific binding partner 34 will bind specifically to the iron biomarker when the iron biomarker is present in the sample (S) applied to first layer 16 to produce an iron complex (IC) of the iron biomarker bound to iron mobile labelled specific binding partner 34. In one example, iron mobile labelled specific binding partner 34 is a RPE-anti-ferritin conjugate that will specifically bind to ferritin molecules, although other binding partners may be utilized for other iron biomarkers.

The label for iron mobile labelled specific binding partner 34 is selected from the group consisting of carbon nano-particles, metallic nano-particles, magnetic nano-particles, fluorophores, quantum dots, and chemiluminescent particles. In one example, the label for iron mobile labelled specific binding partner 34 is R-phycoerythrin (RPE).

Vitamin A mobile labelled specific binding partner 35 is selected to be a binding partner of the vitamin A biomarker, such as RBP, such that vitamin A mobile labelled specific binding partner 35 will bind specifically to the vitamin A biomarker when the vitamin A is present in the sample (S) applied to first layer 16 to produce vitamin A complex (VAC) of the vitamin A biomarker bound to vitamin A mobile labelled specific binding partner 35. In one example, vitamin A mobile labelled specific binding partner 35 is a FITC-anti-RBP conjugate that will specifically bind to RBP molecules, although other binding partners may be utilized for other vitamin A biomarkers.

The label for vitamin A mobile labelled specific binding partner 35 is selected from the group consisting of carbon nano-particles, metallic nano-particles, magnetic nano-particles, fluorophores, quantum dots, and chemiluminescent particles. In one example, the label for vitamin A mobile labelled specific binding partner 35 is fluorescein (FITC), such that iron mobile labelled specific binding partner 34 and vitamin A mobile labelled specific binding partner 35 have different color fluorophore labels. In other examples, iron mobile labelled specific binding partner 34 and vitamin A mobile labelled specific binding partner 35 may have the same color fluorophore labels.

In one example, first layer 16 also includes inflammation mobile specific binding partner 36 located therein. Inflammation mobile labelled specific binding partner 36 is selected to be a binding partner of the inflammation biomarker, such as CRP, such that inflammation mobile labelled specific binding partner 36 will bind specifically to the inflammation biomarker when the inflammation biomarker is present in the sample (S) applied to the first layer 16 to produce an inflammation complex (IFC) of the inflammation biomarker bound to inflammation mobile labelled specific binding partner 36. In one example, inflammation mobile labelled specific binding partner 36 is a PE/Cy5-anti-CRP conjugate that will specifically bind to CRP molecules, although other binding partners may be utilized for other inflammation biomarkers.

The label for inflammation mobile labelled specific binding partner 36 is selected from the group consisting of carbon nano-particles, metallic nano-particles, magnetic nano-particles, fluorophores, quantum dots, and chemiluminescent particles. In one example, the label for inflammation mobile labelled specific binding partner 36 is phycoerythrin/Cyaine5 (PE/Cy5), such that iron mobile labelled specific binding partner 34, vitamin A mobile labelled specific binding partner 35, and inflammation mobile labelled specific binding partner 36 have different color fluorophore labels. In other examples, iron mobile labelled specific binding partner 34, vitamin A mobile labelled specific binding partner 35, and inflammation mobile labelled specific binding partner 36 may have the same color fluorophore labels.

In one example, the labels R-phycoerythrin (RPE), fluorescein (FITC) and phycoerythrin/Cyaine5 (PE/Cy5) are utilized on detection antibodies for ferritin, RBP and CRP fluorescence assay, respectively. The combination of RPE, FITC and PE/Cy5 is suitable for a three-color fluorescence test, because they have similar excitation wave-lengths (~488 nm), but different emission spectra, which peak at 564 nm (RPE), 532 nm (FITC) and 649 nm (PE/Cy5), leading to distinguishable colors: orange, green and red, respectively. Utilizing the fluorescence tags with different colors for different markers advantageously allows for potential cross binding between antibodies to be determined by observing if a fluorescence color appears in the wrong detection area. Also, using a higher quantum yield fluorescence tag on the marker with lower concentration may balance the brightness of each test line and reduce the dynamic range required for detection.

Second layer 18 is supported on substrate 12 proximate to second end 32 of multiplexed diagnostic assay strip 10 and downstream of first layer 16. Second layer 18 is made of a material selected from the group consisting of cellulose and nitrocellulose, although other suitable materials may be utilized. Second layer 18 includes iron test region 38, vitamin A test region 40, and control region 42 separated from each of iron test region 38 and vitamin A test region 40. In one example, second layer 18 also includes inflammation test region 44.

Iron test region 38 operates as a sandwich assay. Iron test region 38 has immobilized specific binding partner 45, in this example anti-ferritin, located therein, which will specifically bind to the iron complex (IC) and immobilize the iron complex (IC) in iron test region 38. Vitamin A test region 40 operates as a competitive assay. Vitamin A test region 40 has immobilized vitamin A biomarker 46, in this example RBP, that will bind to vitamin A mobile specific binding partner 35, which is not bound to the vitamin A biomarker from the sample (S), passing from first layer 16 to second layer 18 and immobilize the unbound vitamin A mobile specific binding partner 35 in vitamin A test region 40. In this example, iron test region 38 and vitamin A test region 40 are spaced apart from one another to assist in analyzing the results, although in other examples iron test region 38 and vitamin A test region 40 may overlap with the results for each being distinguished by different labels. Inflammation test region 44, which is optional, operates as a sandwich assay. Inflammation test region 44 has immobilized specific binding partners 47, in this example anti-CRP, located therein, which will specifically bind to the inflammation complex (IFC) and immobilize the inflammation complex (IFC) in inflammation test region 44.

Because serum RBP concentrations (>20 µg/mL or 0.95 µmon in healthy group) can be ~10 times higher than serum CRP concentrations (<3 µg/mL or 0.12 µmon for healthy people), and ~105 times higher than serum ferritin concentrations (<15 ng/mL or 33 pmol/L for iron deficiency), the combination of a sandwich ferritin assay, a competitive RBP assay, and a sandwich CRP assay on multiplexed diagnostic assay strip 10 allows the entire physical range of the three biomarkers to be covered with a single assay.

Control region 42 has immobilized moieties 48(1)-48(n) located therein which will non-specifically bind to iron mobile labelled specific binding partner 34, vitamin A mobile labelled specific binding partner 35, and optionally inflammation mobile labelled specific binding partner 36 and immobilize them in control region 42. Immobilized moieties 48(1)-48(n) may include a species specific anti-immunoglobulin reagent such as an anti-mouse, anti-horse, anti-bovine, anti-rat, anti-sheep, anti-goat, and anti-chicken antibody or various aptamers, including, but not limited to, non-specific protein and nucleic acid aptamers. Although control region 42 is described, a plurality of control regions including different immobilized moieties thereon. In one example, iron test region 38, vitamin A test region 40, inflammation test region 44, and control region 38 include a signal enhancement solution, such as a silver enhancement solution to allow for better imaging and to provide for lower limits of detection, although the signal enhancement solution may alternatively be added by a user.

In one example, multiplexed diagnostic assay 10 optionally also includes one or more spacer layers supported on substrate 12 as described in U.S. Patent Application Publication No. 2018/0273888 and PCT Patent Application WO2017/059436, the disclosures of which are hereby incorporated by reference in their entirety herein. In this example, optional first spacer layer 20 is supported on substrate 12 downstream of first layer 16. In this example, first spacer layer 20 is disposed between first layer 16 and second layer 18 for receiving the sample (S) along with iron complex (IC), vitamin A complex (VAC), and inflammation complex (IFC) formed in first layer 16, although first spacer layer 20 may be supported in other locations along substrate 12. A portion of optional first spacer layer 20 overlaps second layer 18 to provide fluid flow from first spacer layer 20 to second layer 18. In one example, optional first spacer layer 20 is made of high-capacity glass fibers, although other suitable materials may be utilized. In one example, optional first spacer layer 20 is formed from product number GFDX 103000 produced by EMD Millipore, Billerica, Mass.

Optional first spacer layer 20 is designed to substantially stop flow of the material received from first layer 16 within first spacer layer 20 until a further fluid flow is received. By way of example, first spacer layer 20 has a high thickness, high material weight, and a large surface area to maximize the volume capacity of first spacer layer 20. The volume capacity is configured such that the input volume of the sample (S) will be insufficient to overflow first spacer layer 20 in order to reach second layer 18 without further user interaction. In one example, first spacer layer 20 has a thickness of about 0.43 mm and a weight of 75 g/m$^2$. First spacer layer 20 may be cut to dimensions of about 10 mm×4 mm, although the dimensions of first spacer layer 20 may be designed depending on the intended input volume of the sample (S), e.g., a length of first spacer layer 20 may be increased to accommodate a higher input volume, or decreased for a lower input volume.

In order to restart the fluid flow between first spacer layer 20 and second layer 18, the user must introduce a volume of running buffer through buffer pad 14 that fills the remaining volume of first spacer layer 20 and then drives the sample (S) to second layer 18. The dimensions of first spacer layer 20, and in particular the volume capacity, determine the amount of additional fluid, such as a running buffer, that must be added to overflow first spacer layer 20 to deliver the sample (S) to second layer 18 for testing. The ability to substantially stop the sample (S) in first spacer layer 20 allows for arbitrary incubation periods that may be determined by the user as described in further detail below. The delay provides added mixing and incubation time for formation of the iron complex (IC), vitamin A complex (VAC), and inflammation complex (IFC), and allows the user to actively control the incubation period.

Collection layer 22 is supported on substrate 12 downstream of second layer 18 and proximate to second end 32 of multiplexed diagnostic assay strip 10. Collection layer 22 provides an absorbent pad that is designed to receive materials passing through multiplexed diagnostic assay strip 10 to collect the sample (S) for test completion. Collection layer 22 is made of a material selected from the group consisting of cellulose membranes, polyester matrix, glass fiber, and polysulfone membranes.

Another aspect of the present invention relates to a diagnostic assay cartridge including the multiplexed diagnostic assay strip according to the present invention. The diagnostic assay cartridge includes an elongate housing having walls defining a chamber in which the multiplexed diagnostic assay strip is positioned. The cartridge extends between a first end proximate to the first end of the elongate substrate, where the sample is inserted through an inlet passage in a wall of the housing and into the chamber, and a second end proximate to the second end of the elongate substrate at which results of the assay can be assessed.

Referring now to FIG. 1C, multiplexed diagnostic assay strip 10 of the present invention may be housed in diagnostic assay cartridge 50. Diagnostic assay cartridge 50 includes elongate housing 52 having walls 54 defining chamber 56 in which multiplexed diagnostic assay strip 10 is positioned. Chamber 56 is sized to receive multiplexed diagnostic assay strip 10 therein. Diagnostic assay cartridge 50 may be formed of any suitable materials for housing multiplexed diagnostic assay strip 10. Diagnostic assay cartridge 50 extends between first end 58 and second end 60. When multiplexed diagnostic assay strip 10 is located in chamber 56, first end 58 is proximate to first end 30 of elongate substrate 12, while second end 60 is proximate to second end 32 of elongate substrate 12 at which results of the assay can be assessed. Diagnostic assay cartridge 50 includes inlet passage 62 that allows insertion of the sample (S) into chamber 56 and onto first layer 16. Diagnostic assay cartridge 50 also includes viewing portal 64 aligned with iron region 38, vitamin A test region 40, control region 42, and inflammation test region 44 (when present) to allow for analysis of the assay results, such as by imaging iron region 38, vitamin A test region 40, control region 42, and inflammation test region 44 (when present).

Yet another aspect of the present invention relates to a method of conducting a diagnostic assay. The method includes providing a multiplexed diagnostic assay strip in accordance with the present invention. A sample is applied to the first layer. A buffer is applied to the first layer after applying the sample to the first layer, whereby the buffer causes flow of material from the first end of the elongate substrate to the second end of the elongate substrate. The test and control regions in the second layer are analyzed to determine whether the iron biomarker or the vitamin A biomarker are present in the sample and/or what quantity of the iron biomarker or the vitamin A biomarker is present.

First, a multiplexed diagnostic assay strip according to the present invention is provided. In one example, multiplexed diagnostic assay strip 10 is provided, although the method may be utilized with other diagnostic assay strips. Referring again to FIG. 1A, a method is described for an iron and vitamin A deficiency analysis of a blood sample using multiplexed diagnostic assay strip 10 located in diagnostic assay cartridge 50, although other target molecules may be analyzed for other fluid samples. Although the method is described with respect to multiplexed diagnostic assay strip 10 having the capability to also measure the presence of inflammation biomarker, it is to be understood that the method could be performed without measuring the inflammation biomarker.

The user collects a raw blood sample (S) via a finger prick. The sample (S) is applied to inlet passage 62 in cartridge 50 which directs the sample (S) onto first layer 16 of multiplexed diagnostic assay strip 10. In first layer 16, any iron biomarker (ferritin) in the sample (S) specifically binds to iron mobile labelled specific binding partner 34, which in this example is RPE-anti-ferritin conjugate, to produce the iron complex (IC) of the iron biomarker (ferritin) bound to iron mobile labelled specific binding partner 34. Any vitamin A biomarker (RBP) in the sample (S) specifically binds to vitamin A mobile labelled specific binding partner 35, which in this example is FITC-anti-RBP conjugate, to produce the vitamin A complex (VAC) of the vitamin A biomarker (RBP) bound to vitamin A mobile labelled specific binding partner 35. In one example, any inflammation biomarker (CRP) in the sample (S) specifically binds to inflammation mobile labelled specific binding partner 36, which in this example is PE/Cy5-anti-CRP conjugate, to produce the inflammation complex (IFC) of the inflammation biomarker (CRP) bound to inflammation mobile labelled specific binding partner 36.

A running buffer is applied to buffer pad 14 through inlet passage 62 in cartridge 50 after applying the sample (S) to first layer 16. The running buffer may be applied after a sufficient incubation period to enhance the binding for optimal test results. In this example, the running buffer is applied by applying droplets from a dropper bottle after allowing approximately 3 minutes of incubation. The running buffer is added to buffer pad 14 in a sufficient volume to induce a flow of materials between first layer 16 and second layer 18.

In examples where optional first spacer layer 20 is employed, other incubation periods of any length may be utilized due to optional first spacer layer 20 stopping the flow of fluid. The incubation time may be selected to optimize the binding between the biomarkers and the associated mobile labelled specific binding partners. The running buffer is applied in a sufficient volume to cause optional first spacer layer 20 to overflow such that sample (S) including the formed complexes flow from optional first spacer layer 20 to second layer 18. In test strips containing more than one spacer layer, the application of running buffer will be repeated as necessary to reinitiate the flow from the spacer layers. In test strips that do not include any spacer layers, the application of additional running buffer may be omitted.

The iron complex (IC), vitamin A complex (VAC), and inflammation complex (IFC) then flow to optional first spacer layer 20, which as described above has a volume capacity configured such that the input volume of the sample (S) will be insufficient to overflow optional first spacer layer 20. Thus, sample (S) does not reach second layer 18 without further user interaction, although in other examples, the complexes will flow directly from first layer 16 to second layer 18. The ability to substantially stop the sample (S) in optional first spacer layer 20 allows for arbitrary incubation periods that may be determined by the user to allow sufficient binding interactions to occur.

Once in second layer 18, the sample (S) interacts with test regions including iron test region 38, vitamin A test region 40, inflammation test region 44, as well as control region 42. For samples with high ferritin levels, most of iron mobile labelled specific binding partner 34, in this example the RPE-anti-ferritin conjugate, is occupied with ferritin to form the iron complex (IC). The iron complex (IC) binds to the immobilized specific binding partners (anti-ferritin) in iron test region 38 resulting in a greater colorimetric change in iron test region 38.

For samples with high RBP levels, most of the vitamin A mobile labelled specific binding partner 35, in this example FITC-anti-RBP, is occupied with RBP from the initial sample (S) to form the vitamin A complex (VAC), and thus do not interact with immobilized vitamin A biomarker, in this case RBP, located in vitamin A test region 40. This results in only a subtle colorimetric change in vitamin A test region 40. The preoccupied FITC-anti-RBP that pass vitamin A test region 40 without binding are captured by one of immobilized moieties 48(1)-48(n) located in control region 42, resulting in a weak T/C signal intensity for high vitamin A levels in sample (S). For samples with low vitamin RBP levels, vitamin A test region 40 develops an intense color reflecting the high number of FITC-anti-RBP that bind with immobilized RBP in vitamin A test region 40. This leads to a weak signal in control region 42 due to the depleted number of FITC-anti-RBP reaching control region 42 and, consequently, strong T/C signal intensity for low RBP levels in the sample (S).

Next, the complexes present in second layer 18 may optionally be amplified prior to analyzing test region 36 and control region 40. By way of example, a silver enhancement solution may be applied to enhance the colorimetric signals in test regions 38, 40, and 44 and control region 42. The silver enhancement may be applied after a delayed period of time, such as approximately 6 minutes, to allow for sufficient colorimetric development prior to amplifying the complexes present.

Iron test region 38, vitamin A test region 40, and control region 42 are analyzed to determine whether the iron biomarker, such as ferritin, and the vitamin A biomarker, such as RBP, are present in the sample (S). Iron test region 38, vitamin A test region 40, and control region 42 may be further analyzed to determine a quantity of the iron biomarker and the vitamin A biomarker present in the sample (S). Specifically, iron test region 38, vitamin A test region 40, and control region 42 may be imaged and the obtained images processed based on the colorimetric signals to obtain a quantification of the iron biomarker and the vitamin A biomarker in the sample (S). FIG. 1B illustrates exemplary fluorescence images demonstrating the following results (from left to right): healthy, iron deficiency, vitamin A deficiency, iron and vitamin A deficiency, infection, and a control.

In one example, iron test region 38, vitamin A test region 40, and control region 42 are analyzed using the methods described in U.S. Patent Application Publication No. 2016/0080548 and PCT Patent Application PCT/US14/12263, the disclosures of which are hereby incorporated by reference in their entirety herein, although other testing methods that employ image processing may be utilized such as commercial lateral assay flow readers, an example of which is the ESEQuant Lateral Flow Reader produced by Qiagen, Germany. Alternatively, the signal can be recorded over time optically with a camera, photomultiplier, or similar optical sensor. The images are then processed to provide a quantitative analysis of the amount of iron biomarker and vitamin A biomarker in the sample.

In one example, the test and control regions are analyzed using raw Bayer image data, although other image analysis techniques may be utilized. In this example, binary data directly extracted from the camera is transformed to a raw image, followed by cropping dark edges so that only the test strip in the image remains. Then, the image is converted to grayscale and integration of grayscale value in the direction vertical to the flow is performed, so as to reduce the 2D image to a 1D array. Next, the locations of test and control lines are determined. At each of these locations, a polynomial fitting of points is performed to find the brightness of background. The background is then subtracted from the original brightness profile in order to find the true brightness of the control and test lines, which represents the intensity of the fluorescence signal on the test strip. Using the raw image data advantageously eliminates variabilities based on the camera device, such as auto color correction in the camera.

Next, the quantity of the iron biomarker in the sample (S) is used to determine whether there is an iron deficiency in the sample (S) based on the detected quantify of ferritin in the sample (S). The normal range of ferritin in serum is between 15 ng/mL (32 pmol/L) to 150 ng/mL (316 pmol/L) for females or 200 ng/mL (421 pmol/L) for males, while the cut-off for depleted iron storage in children less than 5 years old is <12 ng/mL (26 pmol/L), and <30 ng/mL (63 pmol/L) if inflammation presents.

Next, the quantity of the vitamin A biomarker in the sample (S) is used to determine whether there is a vitamin A deficiency in the sample (S) based on the determined amount of RBP in the sample (S). Different RBP cutoffs such as 14.5 µg/mL (0.69 µmol/L), 14.7 µg/mL (0.70 µmol/L) and 17.4 µg/mL (0.83 µmol/L) may be utilized for a diagnosis of vitamin A deficiency, because the molar ratio between retinol and RBP depends on many factors. In one example, a serum RBP concentration lower than 14.7 µg/mL (0.70 µmol/L) may be employed to determine a vitamin A deficiency. This cut-off corresponds to the diagnostic standard for vitamin A deficiency at 0.70 µmon of serum retinol concentration, assuming a 1:1 retinol to RBP ratio in circulation.

Optionally, inflammation test region 44 and control region 42 are analyzed to determine whether the inflammation biomarker, such as CRP, is present in the sample (S). Inflammation test region 44 and control region 42 may be further analyzed to determine a quantity of the inflammation biomarker present in the sample (S). Inflammation test region 44 is analyzed in the same manner as described above with respect to iron test region 38 and vitamin A test region 40. A challenge to diagnosing iron deficiency and vitamin A deficiency is that RBP and ferritin are both acute phase proteins, which means that RBP concentrations in blood can be temporarily reduced and ferritin concentrations can be temporarily increased by acute infection and inflammation. Therefore, readings taken during acute infection or inflammation periods can result in a false deficiency/sufficiency diagnosis. As such, C-reactive protein (CRP) or similar markers of inflammation should also be measured, to correctly interpret iron and vitamin A status. For people with moderate infection, serum CRP concentration is usually higher 5.0 µg/mL (200 nmol/L), while for healthy people, serum CRP concentration is usually lower than 3.0 µg/mL (120 nmol/L).

The results of the method are then displayed, such as on the screen of a mobile computing device. An exemplary results report is illustrated on a smart phone screen in FIG. 2F.

EXAMPLES

Example 1—Multiplexed Micronutrient Deficiency Test Strip Architecture and Testing Procedure Tests were performed using a disposable custom multiplexed fluorescence test strip that measures ferritin, RBP and CRP concentrations. The test strip consists of: a buffer pad that accepts running buffer, an incubation pad that incubates sample with labeled antibodies, a mixing pad, a nitrocellulose membrane with immobilized anti-CRP, RBP protein, anti-ferritin and secondary antibodies sequentially in the direction of flow, and another cellulose fiber pad to collect the waste sample at the end. To simplify operation an incubation pad is incorporated in the test strip as a substitute for the sample and conjugation pads traditionally used in lateral flow test strips. The incubation pad is pre-loaded with labeled antibodies, allowing pre-incubation of the sample and labeled antibodies immediately as soon as the sample was added.

To perform the test, first 15 μL of human serum was added on the incubation pad and the test strip was left in a light free environment for 3 minutes. Then 60 μL running buffer was added to the buffer pad in order to initiate the flow. The flow front first reaches the CRP test line, then the RBP test line, and then the ferritin test line on the nitrocellulose membrane. All conjugation antibodies are mouse monoclonal antibodies, so goat anti-mouse secondary antibodies are dispensed as control line for all three markers. After a test is performed, fluorescence tags are bound on the test lines and the intensities of fluorescence light for each marker is related to the concentration of the marker in the sample. Those conjugation antibodies that are not captured by the test lines are captured by the secondary antibodies in the control line. Therefore, the color on the control line is a mix of green, orange and red emitted light. The control line demonstrates that the test worked properly and helps locate the position of test lines in the image, because the distance between lines on the image is fixed.

Example 2—Reader and Fluorescence Imaging System

Figure 2A:
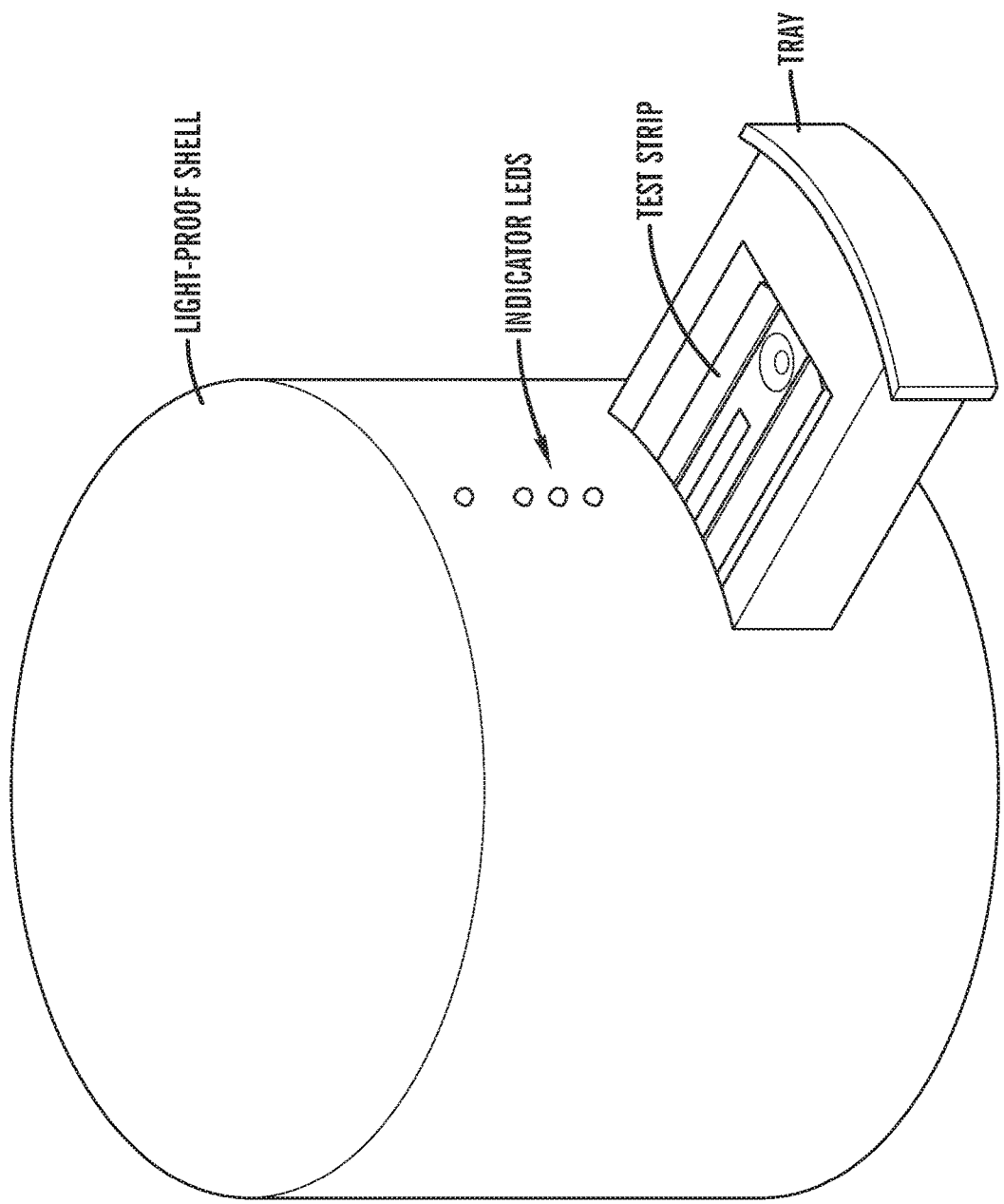
FIGS. 2A and 2B illustrate an exemplary reader used to evaluate results of the multiplexed diagnostic assay strip of the present invention.
Figure 2B:
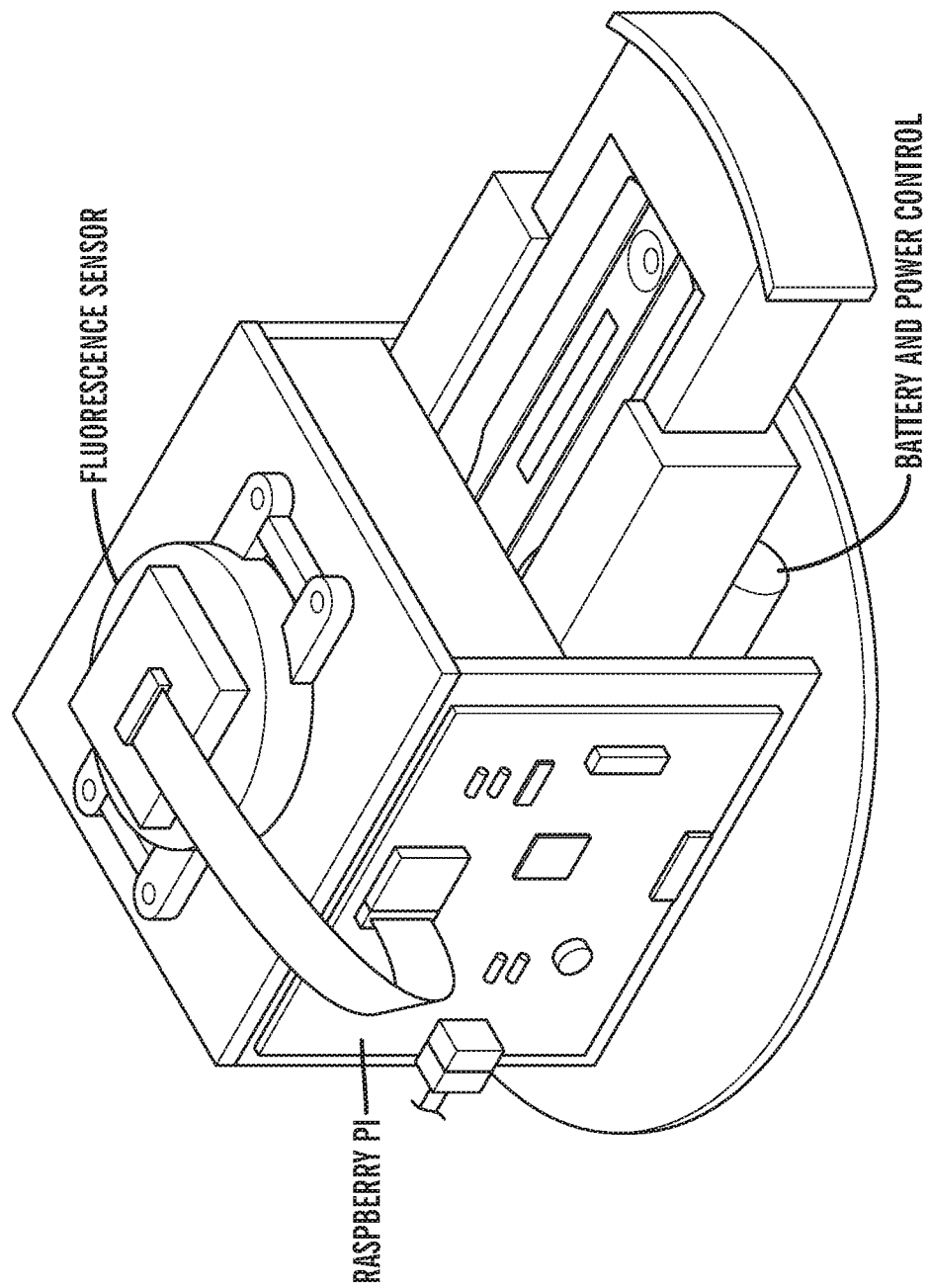

FIGS. 2A and 2B show the design of an exemplary reader device that was used to analyze the assay. The reader links up with a standard laptop or the technology disclosed in U.S. Patent Application Publication No. 2016/0080548 and PCT Patent Application PCT/US14/12263, the disclosures of which are hereby incorporated by reference in their entirety herein, to interpret the results and display them to the user.

Figure 2C:
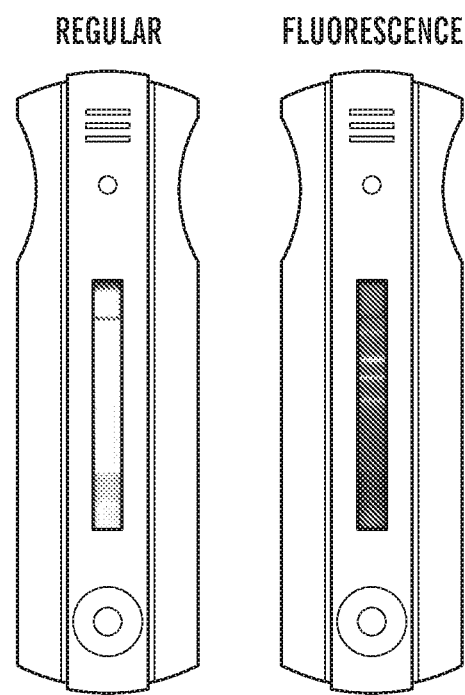
FIG. 2C illustrates an exemplary strip before (in normal indoor ambient light) and after fluorescence.
Figure 2D:
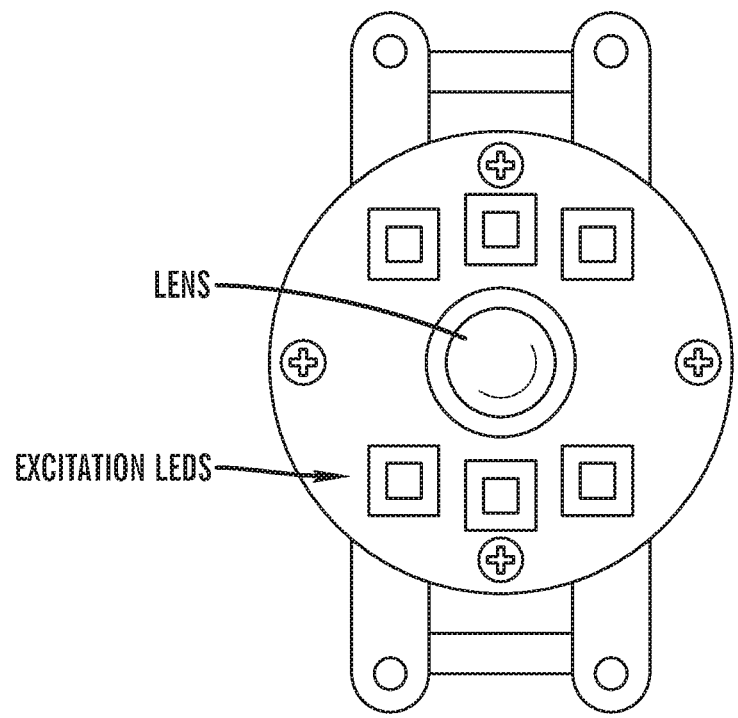
FIG. 2D illustrates an exemplary assembled integrated fluorescence sensor.

In the reader, a tray is built to accept test strip cartridges with a variety of shapes. As shown in FIG. 2C, fluorescence signals appear on the test strip only during fluorescence imaging mode. FIG. 2D shows the design of the fluorescence detection system. The sensor was developed using a Raspberry Pi camera module and is controlled by software using the PiCamera open source library. The sensor excites the fluorescence signal on the test strip using six blue LEDs covered by band pass optical filters with a center wavelength at 458 nm. The LEDs light were filtered by band pass optical filter to reduce background noise in the fluorescence images. A focusing lens with f=25 mm is aligned to the optical path of the camera. A 535 nm long pass optical filter covers the camera to eliminate excitation light. The detection area on the test strip is aligned to the optical path of the sensor in order to maximize image quality.

Figure 2E:
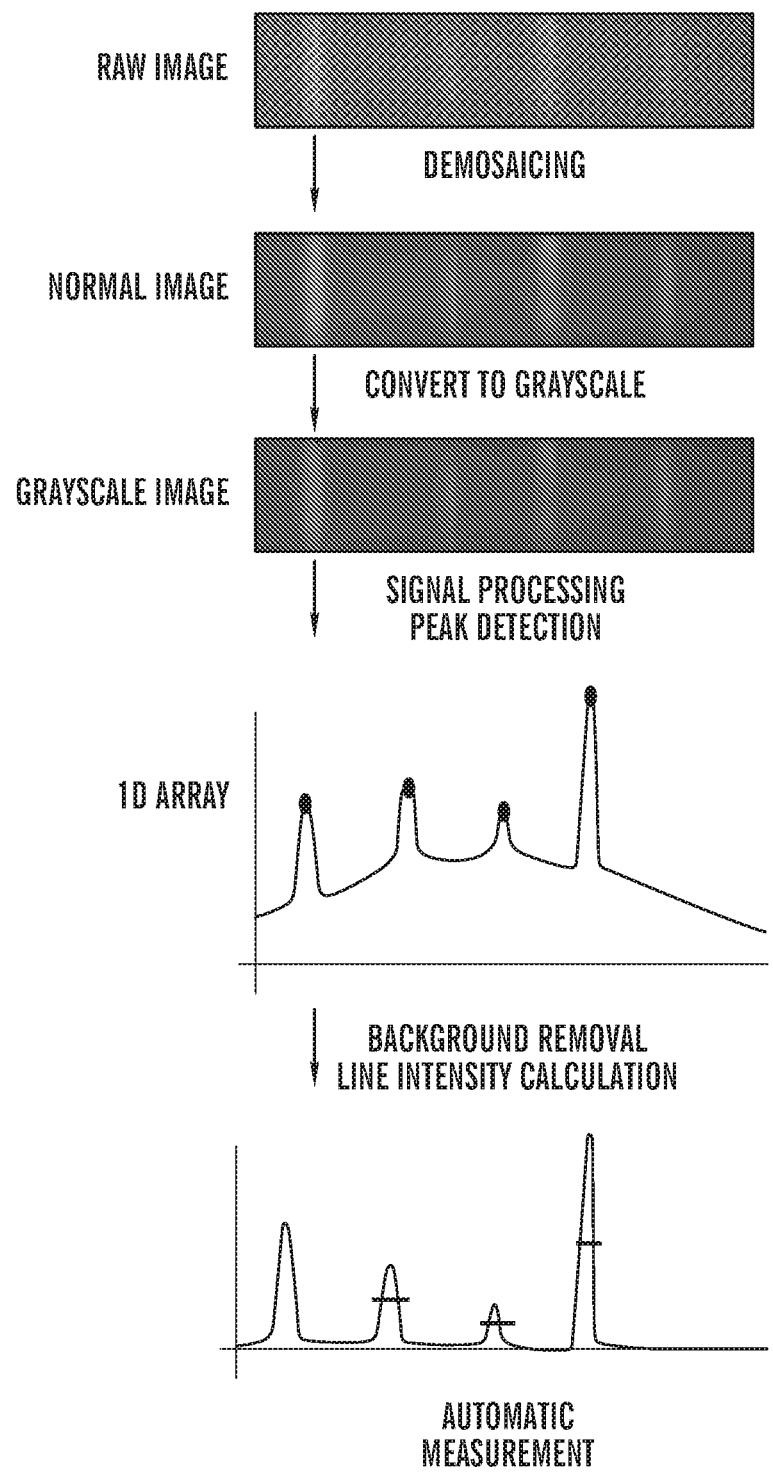
FIG. 2E illustrates an exemplary image processing algorithm used in conjunction with the present invention.
Figure 2F:
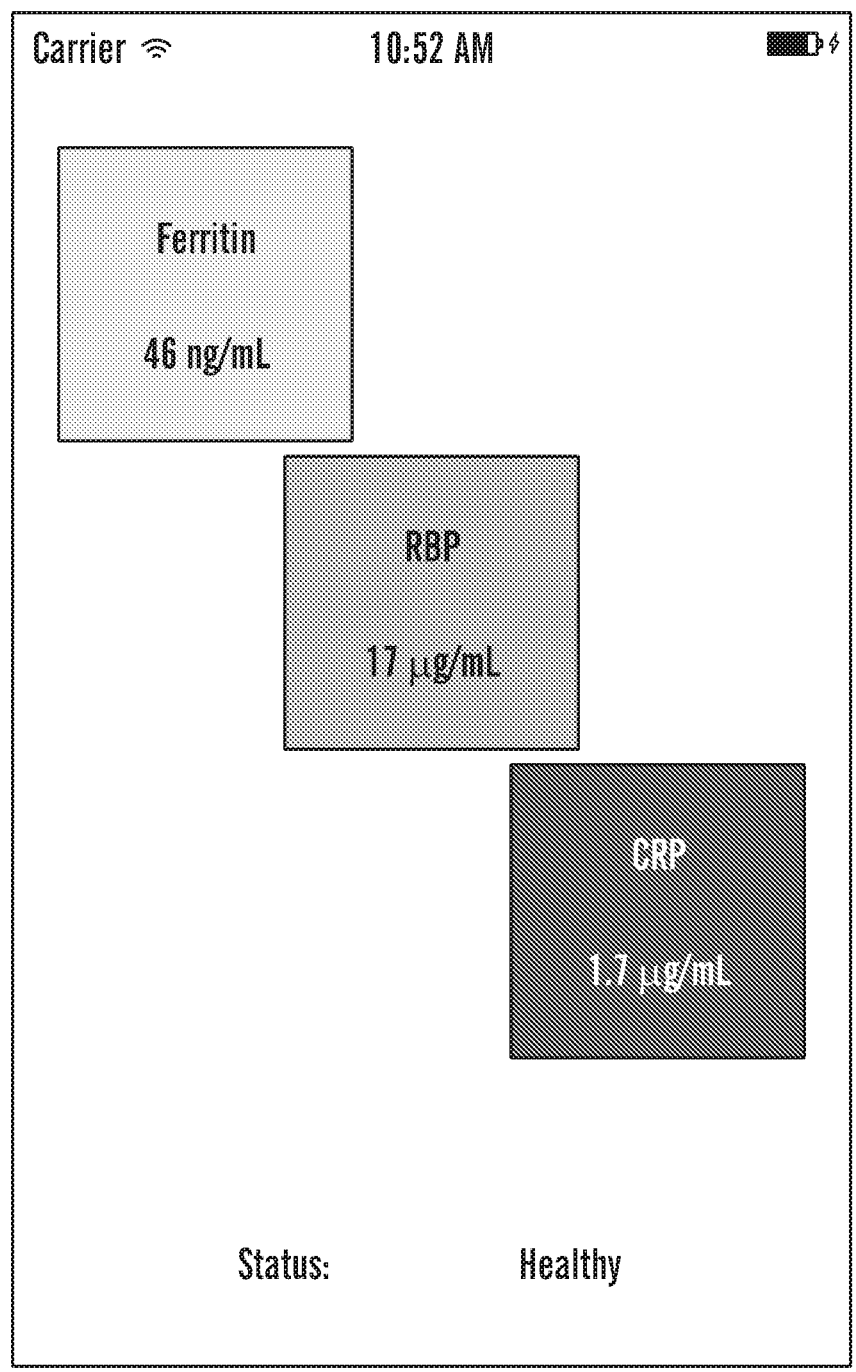
FIG. 2F is an exemplary screenshot of smartphone results page from using the present invention.

To avoid variability introduced by the camera auto correction, the image processing software measures biomarker concentrations with unprocessed raw data directly from the CMOS sensor. FIG. 2E shows the algorithm whereby the captured image is processed and the results are quantified. Briefly, binary data directly extracted from the camera is transformed to a raw image, followed by cropping dark edges so that only the test strip in the image remains. Then, the image is converted to grayscale and integration of grayscale value in the direction vertical to the flow is performed to reduce the 2D image to a 1D array. Next, locations of test and control lines are determined. At each of these locations, a polynomial fitting of points is performed to find the brightness of background. The background is then subtracted from the original brightness profile in order to find the true brightness of the control and test lines, which represents the intensity of the fluorescence signal on the test strip. The average brightness value of each test line is then stored. Finally, the result is displayed on screen, as shown in FIG. 2F.

If concentration of a given marker falls within a physiologically relevant dynamic range, the reader device provides quantitative analysis for all three biomarkers. Otherwise, the reader device tells whether the concentration of biomarkers is greater than the upper bound, or less than the lower bound of the test range. The reader device has a 16 GB SD card as storage. Results are stored in both the reader device and the mobile device after each test, and all previous results can be read at any time.

Figure 3A:
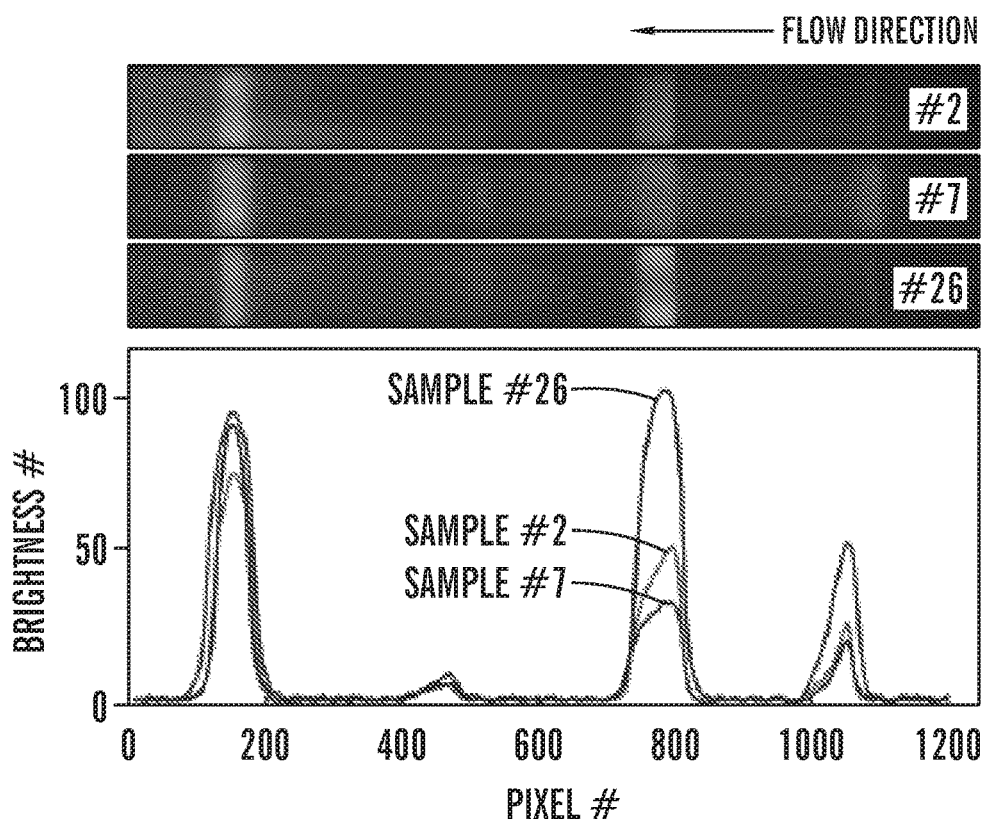
FIGS. 3A-3D illustrate figures used for calibration of the test based on the biomarkers utilized including the colorimetric variation of the multiplex test strip from three different human serum samples: sample 2 (ferritin=34 ng/mL or 75 pmol/L, RBP=16.0 µg/mL or 0.76 µmon and CRP=0.37 µg/mL or 15 nmol/L), sample 7 (ferritin=42 ng/mL or 93 pmol/L, RBP=31.5 µg/mL or 1.48 µmon, and CRP=3.41 µg/mL or 136 nmol/L), sample 26 (ferritin=40 ng/mL or 89 pmol/L, RBP=11.0 µg/mL or 0.52 µmon, and CRP=0.27 µg/mL or 11 nmol/L) (FIG. 3A) and data points showing the average intensity of the fluorescence signal for each marker at different concentration and calibration of each marker (FIGS. 3B-3D). The error bars show the range of values obtained from three test strips with same sample.

Example 3—Ferritin, RBP and CRP Assay Quantification 43 human whole blood samples from different participants were used to quantify the assay. The blood samples were purchased from a commercial source (Research Blood Components, LLC), and were all from US adult donors with no appearance of infectious disease. Concentrations of ferritin, CRP and RBP in the samples were characterized with commercial ELISA kits (Abcam, Inc.). No data was excluded. Four batches of test strips were manufactured and randomly selected for each test. The test strips were stored in light-free environment at room temperature until used. No significant batch to batch variability between test strips was observed, and storage up to 6 weeks had no noticeable effect on the test result. Human serum samples were separated with a portable centrifuge from whole blood and then used as direct input in to the test. FIG. 3A shows the colorimetric variation of test lines from three different human serum samples with known ferritin, RBP and CRP concentration, and their brightness profile acquired by the imaging processing algorithm. The images of strip were rescaled to 40% along the direction vertical to the flow.

Figure 3B:
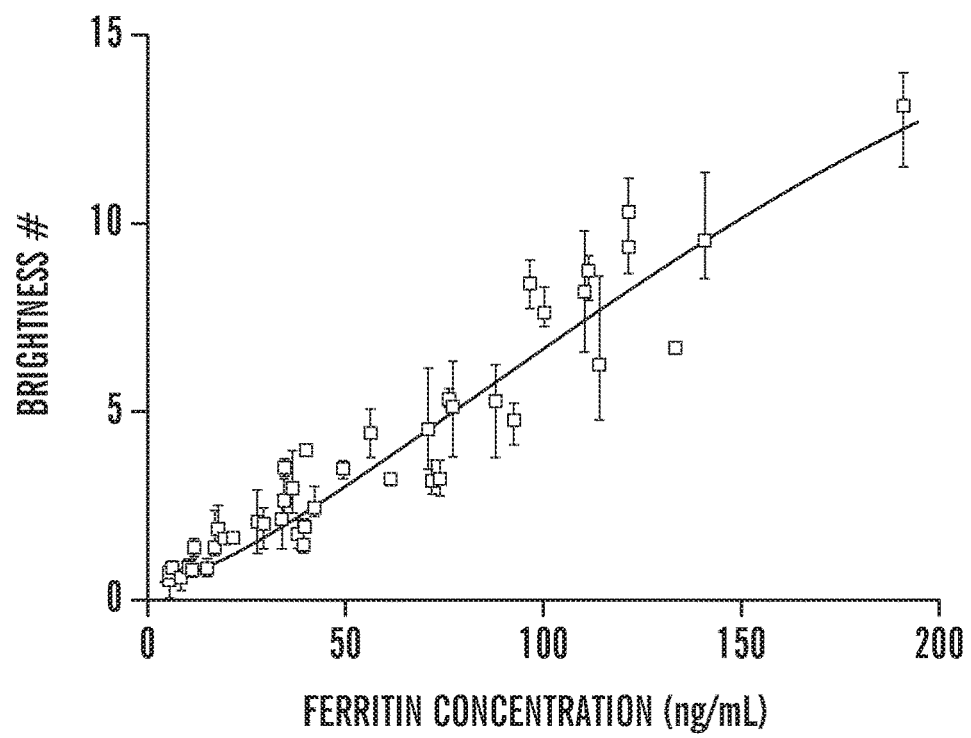
Figure 3C:
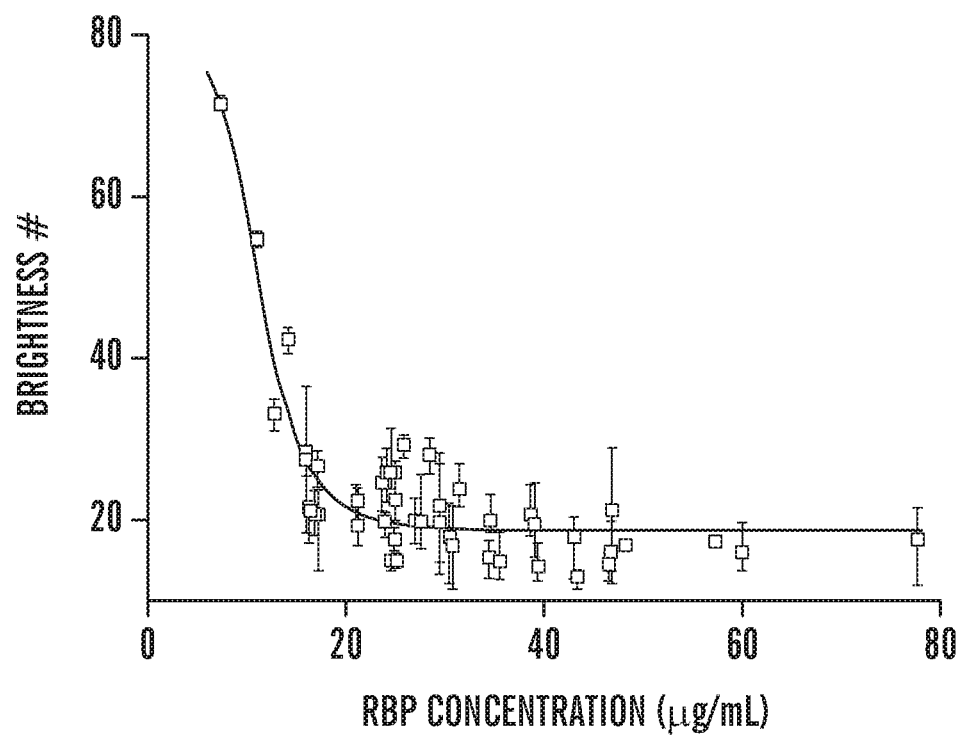
Figure 3D:
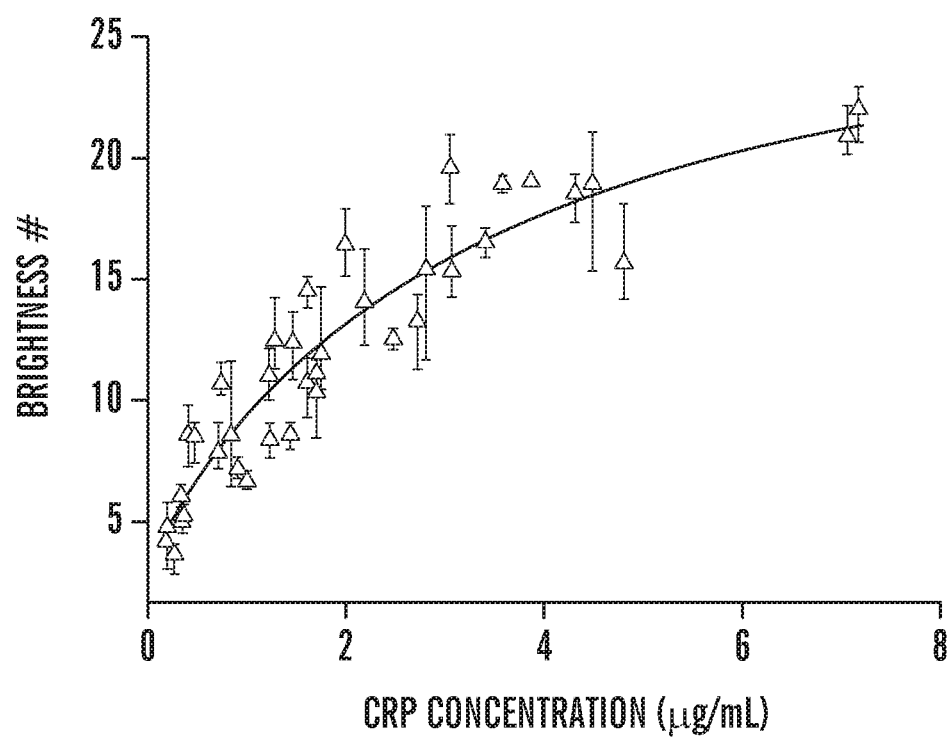

Brightness values of test lines were then correlated to the readout of commercial ELISA kits, as shown in FIGS. 3B-3D. For each of the 43 human samples, 3 test strips were used. The brightness values are averaged for the 3 test strips and range of the brightness values is shown as error bars. According to the ELISA results, 9 out of 43 (20.9%) participants were iron deficient, 4 out of 43 (9.3%) participants were vitamin A deficient, while 10 out of 43 (23.2%) participants were subject to minimal or moderate inflammation. Four-parameter logistic curves were then fitted on each marker such that [marker]=f(brightness), and the calibration functions were stored to predict concentration of each marker in the microcontroller software. Four parameter curve fitting results show $R^2$=0.93 (P<0.0001) for ferritin, $R^2$=0.92 (P<0.0001) for RBP and $R^2$=0.90 (P<0.0001) for CRP. The system shows high accuracy in predicting biomarker concentration based on the fitting curve.

The fitting curve for ferritin shows good linearity within the whole physiological range (15~200 ng/mL or 33~421 pmol/L). The fitting curve for CRP indicates moderate saturation effect at higher concentration (>3 µg/mL or 120 nmol/L), however no hook-effect was observed in this study. For the RBP assay, the RBP assay was optimized to maximize its capability to distinguish vitamin A deficiency (RBP<14.7 µg/mL, or <0.70 µmol/L), and thus compromised on its performance in quantifying RBP concentrations higher than 25 µg/mL (1.19 µmol/L) which still falls in the healthy range.

Example 4—System Performance Evaluation

Figure 4A:
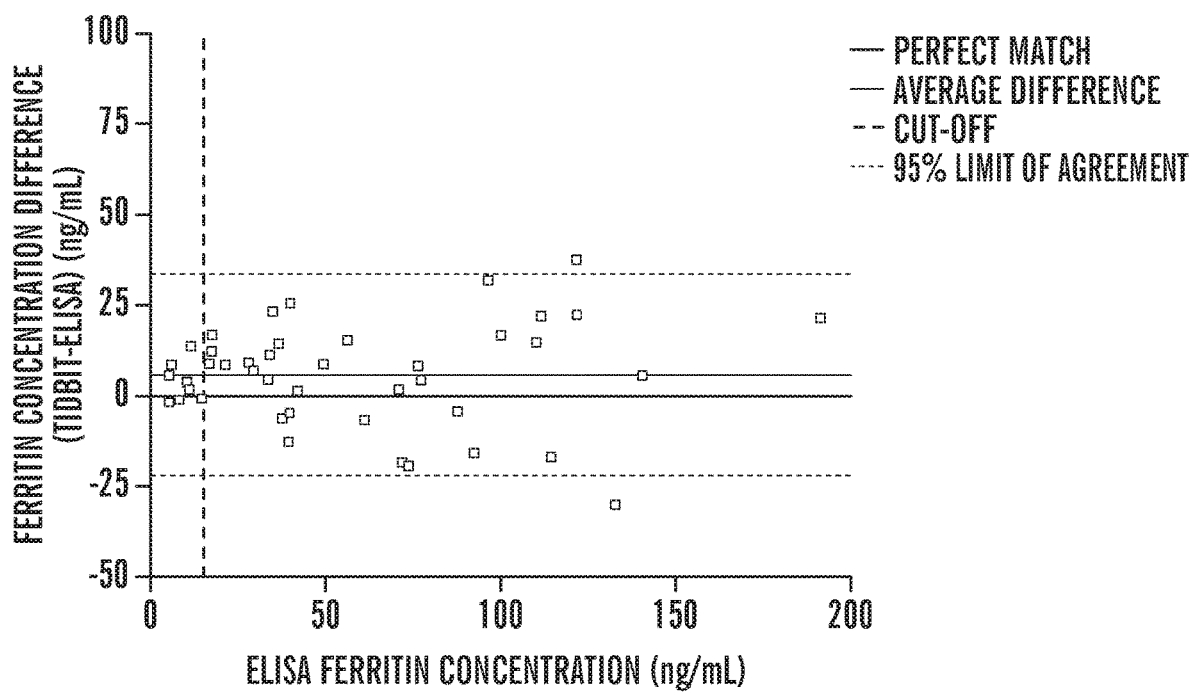
FIGS. 4A-4C are graphs illustrating a comparison between an ELISA's and the present invention's characterization of the concentration of biomarkers including a Bland-Altman plot for the ferritin test (FIG. 4A); a Bland-Altman plot for the RBP test (FIG. 4B); and a Bland-Altman plot for the CRP test.
Figure 4B:
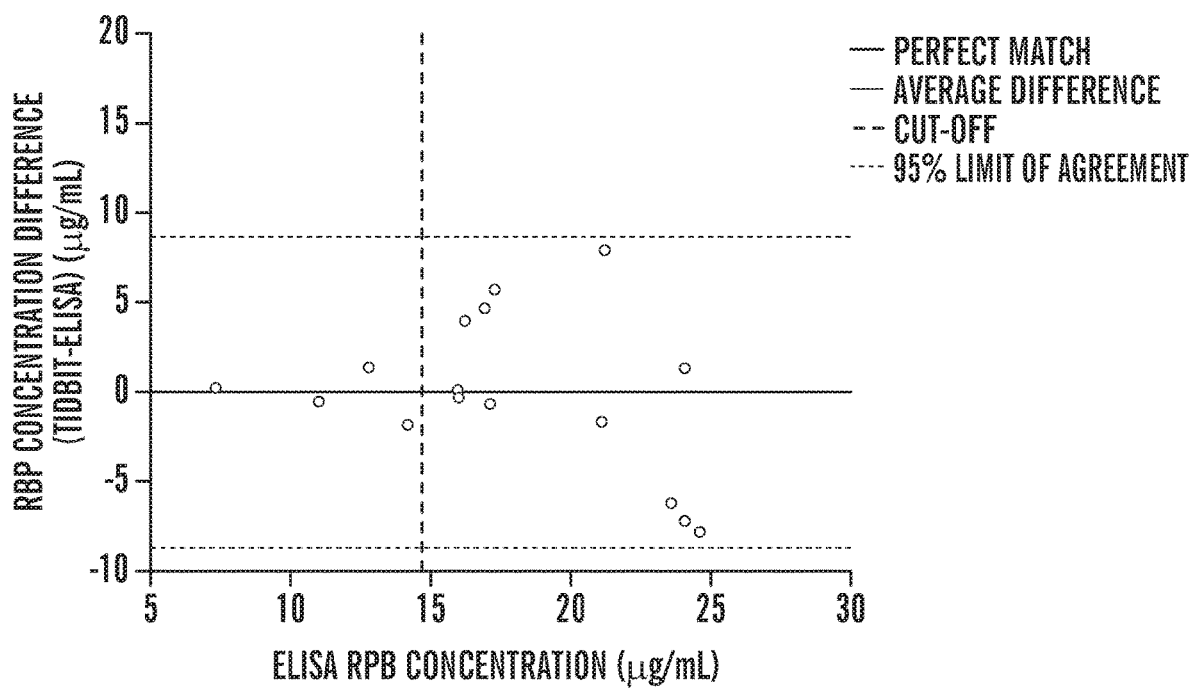
Figure 4C:
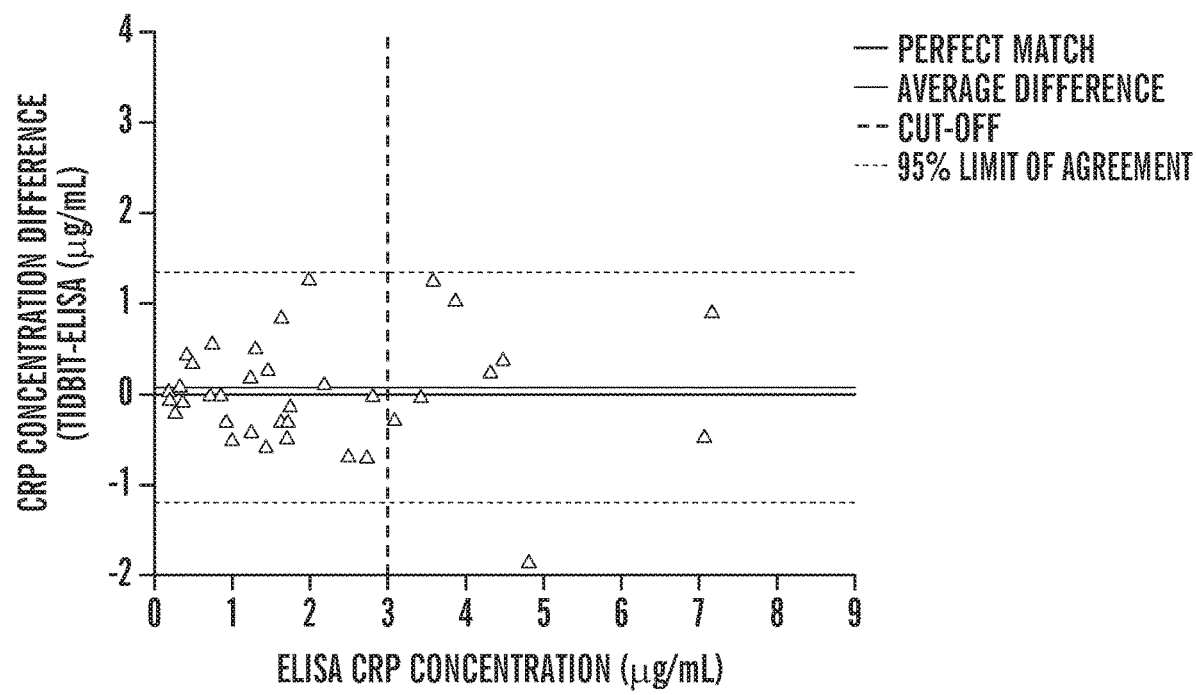

Performance of the system was evaluated by comparing the concentration of the biomarkers acquired by the reader device, and concentration of biomarkers determined with laboratory standard ELISA kits. as shown in FIGS. 4A-4C, in Bland-Altman plots. Linear regression was also applied for each biomarker. Predicted results from the reader device are highly correlated with results from standard methods. Compare to a perfect match with regression coefficient (RC) equal to 1, the ferritin assay shows RC close to a perfect match at +1.06 ($\sigma$=0.03, P<0.0001), with root mean squared error (RMSE) at 14.4 ng/mL (32 pmol/L) and $R^2$ at 0.92, while the CRP assay has RC at +1.03 ($\sigma$=0.04, P<0.0001), with RMSE at 0.65 µg/mL (26 nmol/L) and $R^2$ at 0.88. For the RBP test, because it is a competitive assay and the RBP assay was optimized to maximize its accuracy around the diagnostic threshold (14.7 µg/mL or 0.70 µmol/L), the test line intensity remains low at higher RBP concentration (>25 µg/mL or 1.19 µmol/L) as expected. As a result, in the interface that presents a diagnostic conclusion, the qualitative results are shown instead of the predicted RBP concentration for values greater than 25 µg/mL (1.19 µmol/L) (FIG. 4F). For samples with actual RBP concentration less than 25 µg/mL (1.19 µmol/L), the RBP assay has RC at +0.97 ($\sigma$=0.05, P<0.0001), with RMSE at 4.34 µg/mL (0.21 µmol/L) and $R^2$ at 0.56. Samples with RBP values above the quantitative range are excluded from FIG. 4B.

The reader device system with the multiplexed diagnostic assay strips yielded a sensitivity and specificity at 88% (95% CI 47.3 to 99.6) and 97% (95% CI 85.0 to 99.9) for ferritin, 100% (95% CI 39.7 to 100.0) and 100% (95% CI 90.9 to 100.0) for RBP, 80% (95% CI 55.5 to 99.7) and 97% (95% CI 84.2 to 99.9) for CRP. Moreover, in order to maximize the overall diagnostic accuracy of the system, the cutoff for iron deficiency, vitamin A deficiency and inflammation can be set to ferritin concentration less than 27 ng/mL (60 pmol/L), RBP concentration less than 14.7 µg/mL (0.70 µmol/L), and CRP concentration greater than 2.8 µg/mL (112 nmol/L). Under these conditions the present technology then yielded a 100% (95% CI 59.0 to 100.0) sensitivity and 95% (95% CI 81.3 to 99.3) specificity for ferritin, 100% (95% CI 39.7 to 100.0) and 100% (95% CI 90.9 to 100.0) for RBP, and yielded a 100% (95% CI 66.3 to 100.0) sensitivity and 94% (95% CI 80.3 to 99.2) specificity for CRP.

Example 5—Cross Binding and Limit of Detection Quantification

Figure 5A:
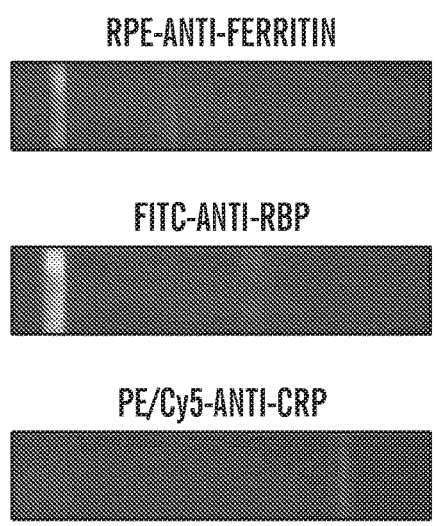
FIG. 5A shows a fluorescence image series for an assay with only one type of conjugation antibodies preloaded.

Cross binding is a factor that can cause potential error in multiplexed lateral flow assays. With the multi-colored fluorescent test strips of the present technology, cross-binding can be easily accounted for since the incorrect florescence signal can be detected at the improper detection site. To demonstrate the level of cross-binding in the present technology, human serum tests were run with only one type of antibody conjugation loaded on the incubation pad. The result is shown in FIG. 5A, which shows that test lines only capture their target biomarkers, proving that non-specific cross binding between antibodies and markers is limited.

Figure 5B:
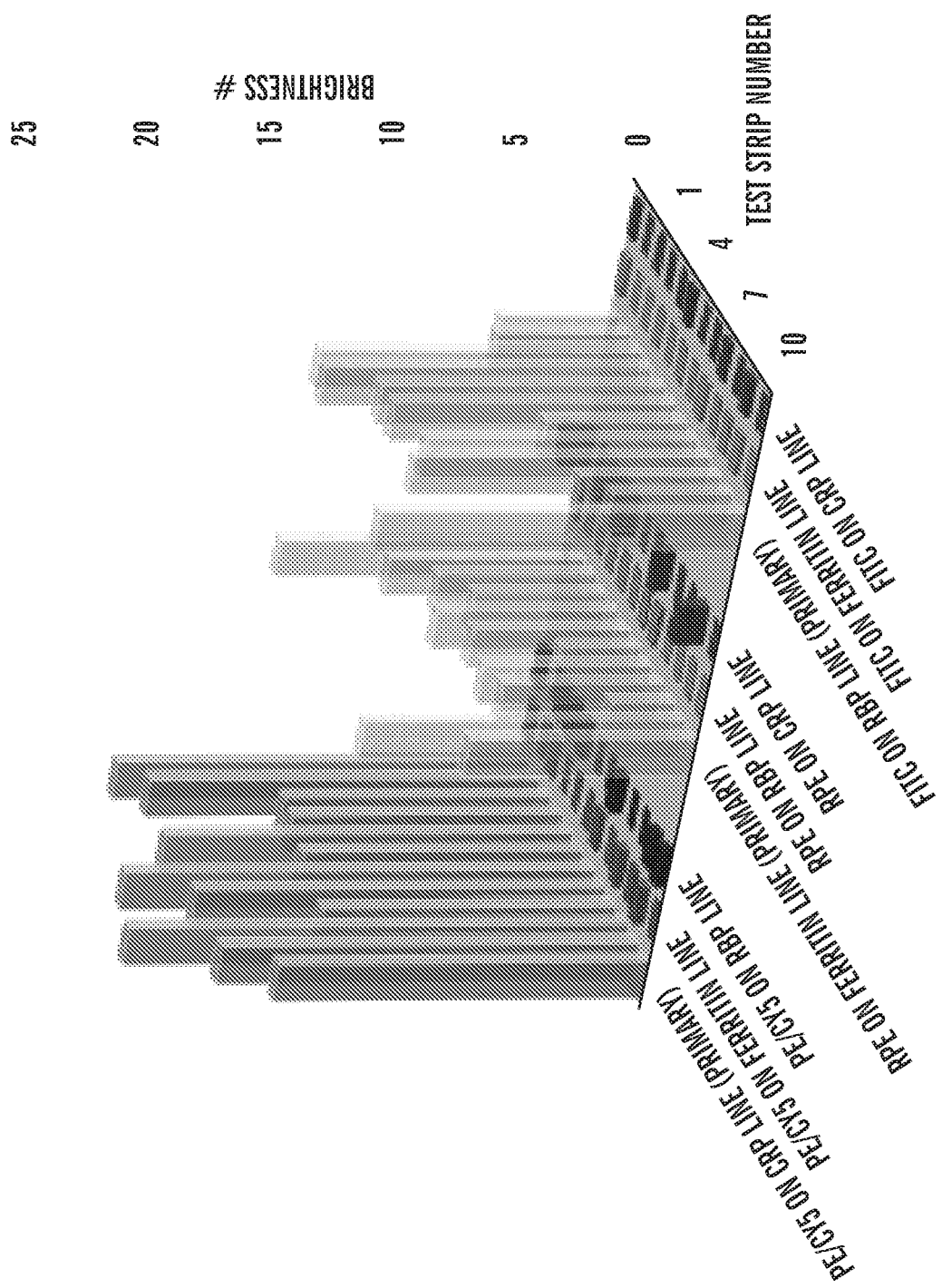
FIG. 5B shows a graph including an evaluation of cross-binding level within 12 human serum sample.

Furthermore, to demonstrate that cross-binding has only a small effect on readout, levels of cross-binding were tested in 12 human serum samples, as shown in FIG. 5B. For each sample, only one type of antibody conjugation was loaded, and the level of cross-binding was evaluated as the ratio of brightness value on the incorrect test lines to the brightness value of correct test line. Error bars indicates the standard deviation of the cross-binding level. As is shown, cross-binding between all biomarker/test line pairs was limited to less than 2%.

The limit of detection for each biomarker was also evaluated, as shown in FIGS. 5C-5E. Since serum samples with very low ferritin, RBP and CRP are hard to obtain, resuspended standard dried serum (Siemens, Inc.) was used to perform the test. For each data point, 8 test strips were used and the error bar shows standard deviation of the result. The non-zero readout for the ferritin and CRP test line intensity at zero concentration indicates there was some non-specific binding on the corresponding test lines. Based on these results, it was determined that the system of the present technology has limits of detection lower than 10.9 ng/mL (24 pmol/L), 2.2 µg/mL (0.10 µmol/L), and 0.092 µg/mL (3.7 nmol/L) for ferritin, RBP, and CRP, respectively. The limit of detection for all the biomarkers was lower than the diagnostic threshold for both adults and children. For children, an alternative form of the assay could also be developed to optimized sensitivity in their relevant range.

Rapid immunoassay tests for multiple targets are challenging. Current rapid diagnostic tests usually label multiple types of conjugation antibodies with the same optical tags (latex beads or colloidal gold nanoparticles), thus cross binding can be difficult to distinguish. The adoption of a three-color fluorescent assay in the device of the present invention offers a direct advantage in that cross binding can be relatively easily spotted by observing the incorrect florescence signal at a given test site.

The present invention provides a rapid point-of-care test for iron deficiency and vitamin A deficiency by quantitatively measuring ferritin, retinol-binding protein (RBP), and C-reactive protein (CRP) concentrations. The test is enabled by the system of the present invention and provides results in around 15 minutes. The system could have significant impact in areas of the world with high instances of micronutrient deficiencies, by providing a rapid, easy-to-operate tool for population-level micronutrient status surveys in situations that both iron deficiency and vitamin A deficiency need to be diagnosed. If implemented with on-strip blood separation, the system's high sensitivity and specificity will allow it to be further applied to individual-level assessment at point-of-care.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A multiplexed diagnostic assay strip for detection of an iron biomarker and a vitamin A biomarker in a sample, said strip comprising:
   an elongate substrate extending between a first end at which the sample is applied to the strip and a second end at which results of the assay can be assessed;
   a first layer supported on said elongate substrate proximate to the first end of the strip for receiving a liquid sample, said first layer comprising:
     an iron mobile labelled specific binding partner that binds specifically to the iron biomarker from the sample applied to the first layer and produces an iron complex of said iron biomarker bound to the iron labelled specific binding partner; and
     a vitamin A mobile labelled specific binding partner that specifically binds to the vitamin A biomarker from the sample applied to the first layer and produces a vitamin A complex of said vitamin A biomarker bound to the vitamin A labelled specific binding partner; and
   a second layer supported on said elongate substrate proximate to the second end of the strip and downstream of said first layer, said second layer comprising:
     an iron test region that has immobilized specific binding partners that specifically binds to the iron complex and immobilizes the iron complex in the iron test region;
     a vitamin A test region that has immobilized vitamin A biomarker that binds to vitamin A mobile labelled specific binding partner, which is not bound to the vitamin A biomarker, passing from said first layer to said second layer and immobilizes the unbound vitamin A mobile labelled specific binding partner in the vitamin A test region; and
     a control region separated from each of the iron test region and the vitamin A test region, wherein the control region has an immobilized moiety which non-specifically binds to and immobilizes the iron labelled specific binding partner and the vitamin A labelled specific binding partner in the control region, wherein the label for the iron mobile labelled specific binding partner has a higher quantum yield than the label for the vitamin A mobile labelled specific binding partner such that the multiplexed diagnostic assay strip is configured to provide simultaneous quantitative analysis of biomarkers comprising the iron biomarker and the vitamin A biomarker in the sample applied to the multiplexed diagnostic assay strip and configured to achieve detection of the iron biomarker within a 95% limit of agreement with laboratory standard ELISA test results and detection of the vitamin A biomarker within a 95% limit of agreement with laboratory standard ELISA test results with a concentration of iron biomarker having a ranging from about 12 ng/mL to about 200 ng/mL and a concentration of vitamin A biomarker having a ranging from about 2.2 µg/mL to about 25 µg/mL in the sample simultaneously.

2. The multiplexed diagnostic assay strip of claim 1, wherein the iron biomarker is ferritin and the vitamin A biomarker is a retinol binding protein (RBP).

3. The multiplexed diagnostic assay strip of claim 1 further comprising:
   a first spacer layer supported on said elongate substrate downstream of said first layer, said first spacer layer being designed to substantially stop flow of material from the second layer within the first spacer layer until a further fluid flow is provided to achieve added mixing and incubation time for formation of the iron complex and the vitamin A complex.

4. The multiplexed diagnostic assay strip of claim 3, wherein said first spacer layer is made of glass fibers.

5. The multiplexed diagnostic assay strip of claim 3, wherein said first spacer layer comprises the iron mobile labelled specific binding partner and the vitamin A mobile labelled specific binding partner therein.

6. The multiplexed diagnostic assay strip of claim 1, wherein said first layer is made of glass fibers.

7. The multiplexed diagnostic assay strip of claim 1, wherein said second layer is made of a material selected from the group consisting of cellulose and nitrocellulose.

8. The multiplexed diagnostic assay strip of claim 1 further comprising:
   a buffer pad supported on said elongate substrate upstream of said first layer and proximate to said first end of said strip, said buffer pad being designed to receive a buffer solution to initiate a flow of materials between said first layer and said second layer.

9. The multiplexed diagnostic assay strip of claim 1 further comprising:
   a collection layer supported on said elongate substrate downstream of said second layer and proximate to the second end of said strip, said collection layer being designed to receive materials passing through said multiplexed diagnostic assay strip.

10. The multiplexed diagnostic assay strip of claim 9, wherein said collection layer is made of a material selected from the group consisting of cellulose membranes, polyester matrix, glass fiber, and polysulfone membranes.

11. The multiplexed diagnostic assay strip of claim 1, wherein the labels for the iron mobile labelled specific binding partner and the vitamin A mobile labelled specific binding partner are independently selected from the group consisting of carbon nano-particles, metallic nano-particles, magnetic nano-particles, fluorophores, quantum dots, and chemiluminescent particles.

12. The multiplexed diagnostic assay strip of claim 1, wherein each of the iron mobile labelled specific binding partner and the vitamin A mobile labelled specific binding partner has a different color fluorophore label.

13. The multiplexed diagnostic assay strip of claim 1, wherein the iron test region and vitamin A test region are spaced apart from one another in the second layer.

14. The multiplexed diagnostic assay strip of claim 12, wherein the iron label is R-phycoerythrin and the vitamin A label is fluorescein.

15. The multiplexed diagnostic assay strip of claim 1 further comprising:
   an inflammation mobile labelled specific binding partner in the first layer that binds specifically to an inflammation biomarker from the sample applied to the first layer and produces an inflammation complex of the inflammation mobile specific binding partner and the inflammation biomarker, wherein the second layer further comprises an inflammation test region that has immobilized specific binding partners that specifically binds to the inflammation complex and immobilizes the inflammation complex in the inflammation test region.

16. The multiplexed diagnostic assay strip of claim 15, wherein the inflammation biomarker is a C-reactive protein (CRP).

17. The multiplexed diagnostic assay strip of claim 15, wherein the labels for the inflammation mobile labelled specific binding partner, the iron mobile labelled specific binding partner, and the vitamin A mobile labelled specific binding partner are independently selected from the group consisting of carbon nano-particles, metallic nano-particles, magnetic nano-particles, fluorophores, quantum dots, and chemiluminescent particles.

18. The multiplexed diagnostic assay strip of claim 15, wherein each of the iron biomarker mobile labelled specific binding partner, the vitamin A biomarker mobile labelled specific binding partner, and the inflammation biomarker mobile labelled specific binding partner has a different color fluorophore label.

19. The multiplexed diagnostic assay strip of claim 15, wherein the iron test region, the vitamin A test region, and the inflammation test region are spaced apart from one another in the second layer.

20. The multiplexed diagnostic assay strip of claim 15, wherein the iron biomarker label is R-phycoerythrin, the vitamin A biomarker label is fluorescein, and the inflammation marker label is phycoerythrin/Cyaine5.

21. The multiplexed diagnostic assay strip of claim 15 further comprising:
a first spacer layer supported on said elongate substrate downstream of said first layer, said first spacer layer being designed to substantially stop flow of material from the first layer within the first spacer layer until a further fluid flow is provided to achieve added mixing and incubation time for formation of the iron complex, the vitamin A complex, and the inflammation complex.

22. The multiplexed diagnostic assay strip of claim 21, wherein said first spacer layer is made of glass fibers.

23. The multiplexed diagnostic assay strip of claim 21, wherein said first spacer layer further comprises the iron biomarker mobile labelled specific binding partner, the vitamin A biomarker mobile labelled specific binding partner, and the inflammation biomarker mobile labelled specific binding partner therein.

24. The multiplexed diagnostic assay strip of claim 1 further comprising a signal enhancement solution in one or more of the iron test region, the vitamin A test region, or the control region.

25. The multiplexed diagnostic assay strip of claim 24, wherein the signal enhancement solution comprises a silver enhancement solution.

26. The multiplexed diagnostic assay strip of claim 15 further comprising a signal enhancement solution in one or more of the iron test region, the vitamin A test region, the control region, or the inflammation test region.

27. The multiplexed diagnostic assay strip of claim 26, wherein the signal enhancement solution comprises a silver enhancement solution.

28. The multiplexed diagnostic assay strip of claim 15, wherein the label for the inflammation mobile labelled specific binding partner has a higher quantum yield than the label for the vitamin A mobile labelled specific binding partner and a lower quantum yield than the label for the iron mobile labelled specific binding partner.

29. The multiplexed diagnostic assay strip of claim 1, wherein the iron test region operates as a sandwich assay and the vitamin A test region operates as a competitive assay.

30. The multiplexed diagnostic assay strip of claim 15, wherein the iron test region operates as a sandwich assay, the vitamin A test region operates as a competitive assay, and the inflammation test region operates as a sandwich assay.

31. The multiplexed diagnostic assay strip of claim 15, wherein the multiplexed diagnostic assay strip is configured to achieve detection of an inflammation biomarker within a 95% limit of agreement with laboratory standard ELISA test results.

32. The multiplexed diagnostic assay strip of claim 1, wherein the multiplexed diagnostic assay strip is configured to achieve a sensitivity of 100% to the vitamin A biomarker and/or the iron biomarker, and optionally the inflammation biomarker.

33. The multiplexed diagnostic assay strip of claim 1, wherein the multiplexed diagnostic assay strip is configured to achieve average differences from the laboratory standard ELISA test results of less than 10 ng/mL for ferritin, and/or less than 5 µg/mL for retinol-binding protein and/or optionally less than 1 µg/mL for C-reactive protein in the entire physical range of the biomarkers to be covered with a single multiplexed diagnostic assay.

34. The multiplexed diagnostic assay strip of claim 1, wherein the vitamin A test region is positioned closer to the first end than the iron test region such that the liquid sample passes through the vitamin A test region before passing through the iron test region, and wherein the vitamin A test region is configured to carry out a competitive assay and the iron test region is configured to carry out a sandwich assay.

35. The multiplexed diagnostic assay strip of claim 15, wherein the assay strip is capable of detecting a concentration of the inflammation biomarker having a ranging from about 0.5 to 10 µg/mL.

36. A multiplexed diagnostic assay cartridge comprising:
the multiplexed diagnostic assay strip of claim 1; and
an elongate housing having walls defining a chamber in which said multiplexed diagnostic assay strip is positioned, said cartridge extending between a first end proximate to the first end to the elongate substrate, where the sample is inserted through an inlet passage in a wall of the housing and into the chamber, and a second end proximate to the second end of the elongate substrate at which results of the assay can be assessed.

37. A method of conducting a diagnostic assay, said method comprising:
providing the multiplexed diagnostic assay strip of claim 1;
applying a sample to said first layer;
applying a buffer to a buffer pad positioned upstream of said first layer after said applying the sample to said first layer, whereby the buffer causes flow of material from the first end of said elongate substrate to the second end of said elongate substrate; and
analyzing the test and control regions in said second layer to determine whether the iron biomarker or the vitamin A biomarker are present in the sample and/or what quantity of the iron biomarker or the vitamin A biomarker is present.

38. The method of claim 37 further comprising:
determining whether there is an iron deficiency in the sample based on the determined quantity of the iron biomarker in the sample; and
determining whether there is a vitamin A deficiency in the sample based on the determined quantity of the vitamin A biomarker in the sample.

39. The method of claim 37 further comprising:
amplifying the complexes present in said second layer prior to said analyzing.

40. The method of claim 37 further comprising:
displaying the results of said method.

41. The method of claim 37, wherein the analyzing further comprises:
   analyzing the test and control regions in said layer using raw Bayer image data.
42. The method of claim 37 further comprising:
   analyzing the test and control regions in said second layer to determine whether the inflammation biomarker is present in the sample and/or what quantity of the inflammation biomarker is present.

* * * * *